(12) United States Patent
Summar et al.

(10) Patent No.: US 10,792,339 B2
(45) Date of Patent: Oct. 6, 2020

(54) METHODS AND COMPOSITIONS FOR TREATING PHENYLKETONURIA

(71) Applicant: Children's National Medical Center, Washington, DC (US)

(72) Inventors: Marshall Summar, Washington, DC (US); Juan Cabrera-Luque, Washington, DC (US); Gary Cunningham, Washington, DC (US); Dione T. Kobayashi, Boston, MA (US); James G. McArthur, Concord, MA (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 151 days.

(21) Appl. No.: 15/212,009

(22) Filed: Jul. 15, 2016

(65) Prior Publication Data
US 2017/0106054 A1    Apr. 20, 2017

Related U.S. Application Data

(60) Provisional application No. 62/193,952, filed on Jul. 17, 2015.

(51) Int. Cl.
| | |
|---|---|
| *A61K 38/44* | (2006.01) |
| *C12N 9/00* | (2006.01) |
| *A61K 38/51* | (2006.01) |
| *A61K 31/708* | (2006.01) |
| *A61K 31/195* | (2006.01) |
| *A61K 9/48* | (2006.01) |
| *A61K 45/06* | (2006.01) |
| *C12N 9/06* | (2006.01) |
| *A61K 31/7084* | (2006.01) |
| *A61K 9/00* | (2006.01) |

(52) U.S. Cl.
CPC ............ *A61K 38/44* (2013.01); *A61K 9/0053* (2013.01); *A61K 9/4891* (2013.01); *A61K 31/195* (2013.01); *A61K 31/7084* (2013.01); *A61K 38/51* (2013.01); *A61K 45/06* (2013.01); *C12N 9/0014* (2013.01); *C12Y 104/0102* (2013.01); *C12Y 403/01024* (2013.01)

(58) Field of Classification Search
None
See application file for complete search history.

(56) References Cited

U.S. PATENT DOCUMENTS

2017/0198329 A1* 7/2017 Ayyub .................... C12Q 1/32

FOREIGN PATENT DOCUMENTS

| CN | 103555683 A | 2/2014 |
|---|---|---|
| WO | WO 2014/062985 A1 | 4/2014 |
| WO | WO 2015/031911 A1 | 3/2015 |

OTHER PUBLICATIONS

Brunhuber et al., "Rhodococcus L-Phenylalanine Dehydrogenase: Kinetics, Mechanism, and Structural Basis for Catalytic Specifity", Biochemistry 2000, vol. 39, No. 31, pp. 9174-9187.*
Notification of Transmittal of the International Search Report and The Written Opinion of the International Searching Authority for International Application No. PCT/US2016/042622, entitled: "Methods And Compositions For Treating Phenyltonuria", dated Nov. 17, 2016.
Strisciuglio, P. and Concolino, D., "New Strategies for the Treatment of Phenylketonuria (PKU)", *Metabolites*, vol. 4; 1007-1017 (2014).

* cited by examiner

*Primary Examiner* — Suzanne M Noakes
(74) *Attorney, Agent, or Firm* — Ballard Spahr LLP

(57) ABSTRACT

The present invention provides compositions and methods of treating hyperphenylalaninemia (e.g., phenylketonuria) in a subject in need thereof comprising administering to the subject an effective amount of a phenylalanine dehydrogenase (PheDH) polypeptide. The present invention also provides pharmaceutical formulations comprising PheDH for lowering the phenylalanine concentration in the subject (e.g., in the intestines and/or blood).

20 Claims, 21 Drawing Sheets
(15 of 21 Drawing Sheet(s) Filed in Color)
Specification includes a Sequence Listing.

```
WT_GtPheDH    1 ATGAATACCGTTACCAATCAGTGGAAAGCGGTGGATATATTTACGCAAAT  50
                ||||||||||||| ||| ||||  |||||| ||||||||| | ||| ||
CO_GtPheDH    1 ATGAATACTGTGACGAATCAATGGAAAGCTGTGATATCTTTACGCAGAT  50

WT_GtPheDH   51 TCGTGACCATGAGCAAGTCGTATTTGTAATGATAAAAACACGGGATTAA  100
                 | || |||||||| ||||||||| |||  || || |  |||| | |
CO_GtPheDH   51 CCGGGATCATGAACAAGTGTTTCGTAATGATAAGAACACCGGTCTGA   100

WT_GtPheDH  101 AAGCAATTATCGCCATTCATGACAACGTTAGGCCCAGCGCTTGGCGGA   150
                 ||||| |||| |||| ||||  | |||| |||||  | || |||| |
CO_GtPheDH  101 AGGCTATCATCGGATTCACGACGACCACCCTGGGTCCTGCTCTGGGGC   150

WT_GtPheDH  151 TGTCGGATGTACCCATATATGCGACCGTTGAAGAGCCACTATTGATGTGCT  200
                |  | ||| |||||   |  |||| ||||| |||| | || | || ||
CO_GtPheDH  151 TGCCGTATGTACCCGTACGCGACGGTCGAAGATGCCCTGTTCGATGTCCT  200

WT_GtPheDH  201 CCGTCTTTTCGA--AAGGG-ATGACGTATAAATGCCTTGCGCAGATGTAG  247
                 | || || |||    ||    |||||| ||| || |||| ||||| ||
CO_GtPheDH  201 GCGCCT---GAGCAAGGCATGACCTACAAGTGTTTGCAGCTGATGTAG   247

WT_GtPheDH  248 ATTTTGGCGGGGGCAAAGCGGTTATTATCGGAGACCCGCACAAAGACAAG  297
                | ||| | ||||||||||||||| |||||  | |||| || |||||||||
CO_GtPheDH  248 ACTTTGGTGGCGGCAAAGCCGTGATTATCGGCGATCCGATAAAGATAAG  297
```

FIG. 8A

| WT_GtPheDH | 298 | ACACCGGAATTGTTCCGTGCATTTGGCCAGTTTGTTGA-ATCGTTGAATG | 346 |
| CO_GtPheDH | 298 | ACCCCAGAGCTGTTCCGTGCATTTGGTCAGTTTGTGGAGAGC-CTCAACG | 346 |
| WT_GtPheDH | 347 | GCCGGTTTTACACAGGTACTGATATGGGAACGACGCCGGATGATTTCGTT | 396 |
| CO_GtPheDH | 347 | GTCGTTTCTATACGGGTACCGATATGGGTACCACCCGACGACTTCGTG | 396 |
| WT_GtPheDH | 397 | CACGCGGATGAAAGAAACAAACTGCATCGTAGTGTTCCTGAAGAGTATGG | 446 |
| CO_GtPheDH | 397 | CACGCGGATGAAAGAAAGAAACTGCATTGTGGGGTCCGGAAGAGTATGG | 446 |
| WT_GtPheDH | 447 | CGGCAGCGGGCGATTCTTCA--GTACCGACCGCGTTAGGTGTCATTTACGG | 494 |
| CO_GtPheDH | 447 | TGGCTCGGGTGA--CTCCAAGCGTCCGACCGGCATTGGGCGTGATCTACGG | 494 |
| WT_GtPheDH | 495 | TATTCAAGCTACCAATAAAGTGATTTGGGGAAGCGACGAGCTTCATGGAA | 544 |
| CO_GtPheDH | 495 | CATTCAAGCGACCAATAAAGTTATCTGGGGTAGCGACGAACTGCACGGTA | 544 |
| WT_GtPheDH | 545 | AAACGTACGCCATCCAAGGGT-TAGGAAAAGTAGGAAGAAAAGTAGCGGA | 593 |
| CO_GtPheDH | 545 | AGACTTACGCAATCC-AGGGTCTGGGTAAGGTTGGTCGTAAAGTCGCAGA | 593 |

FIG. 8B

```
WT_GtPheDH   594 GCGTTTATTGAAAGAAGGAGCGGACTTGTATGTGTGGATATTCATCCAA 643
                 ||| | ||||| || ||||| | ||||| || || |||||||||| ||
CO_GtPheDH   594 GCGCCTGTTGAAAGAGGGGTGCGACCTGTATGTTTGTGATATTCACCGA 643

WT_GtPheDH   644 CGGCAATTGAAGCGGATTGT-ATCATATGCAAAAAAATTGGGAGCGAACGT 692
                 ||||| ||||| ||||| ||  || |||||||| || |||||||| |||| 
CO_GtPheDH   644 CGGGATTGAAGCGGATCGTGAGC-TATGCGAAAAACTGGGTGCGAATGT 692

WT_GtPheDH   693 AAAAGTTGTACAAGGACGGAAATTTACAGAACAGACGCGGATATATTTG 742
                 ||||||| || ||||| ||||||| ||| ||||| || |||| || ||| 
CO_GtPheDH   693 CAAAGTCGTTCAGGGTACGCGGAAATCTATCGCACCGACGCGGACATTTTCG 742

WT_GtPheDH   743 TTCCATGTGCGGTTCGGCAATGTTGTAAATGATAATACGATACATGTGTTG 792
                 | | ||||| |||||||||||||| | |||||| |||| |||||||| ||
CO_GtPheDH   743 TGCCGTGTGCGGTTCGGCAATGTTCAACGATGTTCAACGATAACACTATTCATGTTCTG 792

WT_GtPheDH   793 AAAGTAAAAGCGGATTGTCCGGTTCCGCCAACAATCAATTACTTGATGTGCG 842
                 ||||| ||||| ||||||| ||||| || |||||| ||||| ||||||| |
CO_GtPheDH   793 AAAGTTAAGGCAATCGTTGGTAGCGGAATAACCAGCTGCTGGACGTGCG 842

WT_GtPheDH   843 CCACGGACAGTGCTGAAAGAGAAAGGAATTTTATACGCGCCAGATTACA 892
                 | |||| |||||||||||||| || |||||| ||| || |||||||||
CO_GtPheDH   843 TCACGGTCAACTGCTGAAAGAAAGGGCATCCTGTATGCCCGGATTACA 892
```

FIG. 8C

```
WT_GtPheDH   893  TCGTTAACGCTGGAGGACTTATTCAAGTAGTCTGATGAGCTGTACGGATTG  942
                  |・|||||・|||||・||・|||・||・|・||・|||・||
CO_GtPheDH   893  TTGTGAACGCCGGTGGCCCTGATCCAAGTCGGCGACGAATTATACGGTCTG  942

WT_GtPheDH   943  AATAAAGAAGCGTGTACTACAAAAACAAAGCGATTTATTCGACGCTCCT    992
                  ||・|||||・||・||・|・|||||||・|||||||・・|||・||||
CO_GtPheDH   943  AACAAAGAGGCGGGTTTTGCAAAGAGACCAAGGCAATCTACAGCACCCTGCT 992

WT_GtPheDH   993  TCATATTTATTCCCGTGCAGAAGCAGAGACCATATCACAACAATCGAAGCAG 1042
                  ・|||・||・||・||・||・||・||・||||||・||・||・||・|-|
CO_GtPheDH   993  GCACATCTACTCTCGTGCCGAGGCAGACCATTACCACCATTGAAGCCG    1042

WT_GtPheDH   1043 CAAACCGTTTTGTGAAGAGCGGTTGCAGCAGGTAGCCGCGCAATGAT     1092
                  |・||||||・|||||||・|||||||・||・||・|||・|||・
CO_GtPheDH   1043 CGAACCGTTTTTGCGAGGAAACGCCTGCAGCAAGCGCAGAGTAATGAC     1092

WT_GtPheDH   1093 TTTTTACGCACCGCAAACAGCCGAAGTGGGATATCCGCCGGTAA        1137 SEQ ID NO: 2
                  ||・|||・||||・|||||||・|||||||・||・||・|||
CO_GtPheDH   1093 TTTTTCACGCACCGTAAACAGCCGAAATGGGATATTCGTCGTTAA       1137 SEQ ID NO: 3
```

FIG. 8D

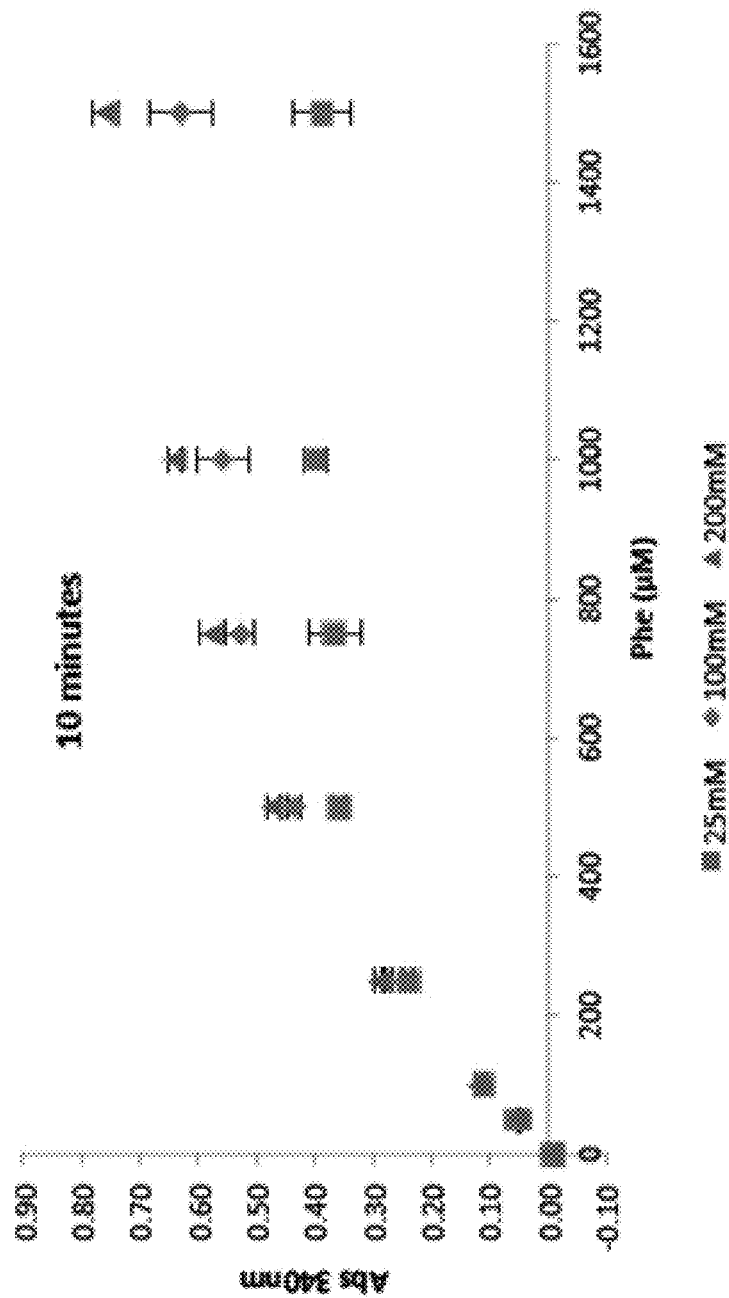

METHODS AND COMPOSITIONS FOR TREATING PHENYLKETONURIA

RELATED APPLICATION

This application claims the benefit of U.S. Provisional Application No. 62/193,952, filed on Jul. 17, 2015. The entire teachings of the above application are incorporated herein by reference.

INCORPORATION BY REFERENCE OF MATERIAL IN ASCII TEXT FILE

This application incorporates by reference the Sequence Listing contained in the following ASCII text file:
  a) File name: 51941000001SEQUENCELISTING.txt; created Sep. 28, 2016, 26 KB in size.

BACKGROUND OF THE INVENTION

Classical phenylketonuria (PKU) is an autosomal recessive disorder caused by deficiencies in phenylalanine hydroxylase (PAH; EC 1.14.16.1) with an incidence of approximately 1:15,000 births in the United States. PKU is characterized by the accumulation of phenylalanine (Phe) in the blood resulting in severe hyperphenylalaninemia (HPA). Affected children manifest mental retardation, seizures, behavioral difficulties, learning disabilities, and other neurological symptoms. High blood Phe levels in PKU patients can be managed by diet. Unfortunately, the difficulties of adhering to a strict diet for life and the presence of subtle or overt neurological deficits make other therapeutic approaches indispensable.

Although a phenylalanine-restricted diet is the cornerstone of treatment for PKU, such diet can lead to imbalances in essential dietary nutrients and a significant decrease in quality of life. This, along with the impracticalities of following the strict diet underscores the need for alternative therapies. However, alternative PKU therapies, such as $BH_4$ treatment, enzyme replacement therapy, large neutral amino acid therapy, and PAH gene therapy, have limited efficacy. For example, $BH_4$ treatment is only effective in about 20% of PAH-deficient patients. In addition, liver-directed gene therapy does not lead to a permanent correction of PAH activity, and enzyme substitution therapy has been proven effective only in mice and only for up to one year with weekly injections.

Accordingly, there is a significant unmet need for more effective therapeutic compositions and methods for treating PKU and other disorders characterized by hyperphenylalaninemia (HPA).

SUMMARY OF THE INVENTION

Described herein are methods and compositions for treating hyperphenylalaninemia (e.g., phenylketonuria). The present invention is based, in part, on the determination that phenylalanine dehydrogenase (PheDH) from the thermophilic bacterium *Geobacillus thermoglucosidasius* (Gt) can reduce phenylalanine levels under conditions similar to the human gastrointestinal tract.

Accordingly, in one aspect, the present invention provides a method of reducing the level of phenylalanine in a subject in need thereof, comprising administering to the subject an effective amount of a phenylalanine dehydrogenase polypeptide, or a functional fragment thereof, wherein the polypeptide has at least about 70% amino acid sequence identity to a wild-type phenylalanine dehydrogenase enzyme from the organism *Geobacillus thermoglucosidasius*.

In another aspect, the present invention provides a method of treating phenylketonuria (PKU) in a subject in need thereof, comprising administering to the subject an effective amount of a phenylalanine dehydrogenase polypeptide, or a functional fragment thereof, wherein the polypeptide has at least about 70% sequence identity to a wild-type phenylalanine dehydrogenase enzyme from the organism *Geobacillus thermoglucosidasius*.

The present invention also provides, in other aspects, a pharmaceutical formulation comprising a pharmaceutically-acceptable carrier and a phenylalanine dehydrogenase polypeptide, or a functional fragment thereof, wherein the polypeptide has at least about 70% sequence identity to a wild-type phenylalanine dehydrogenase enzyme from the organism *Geobacillus thermoglucosidasius*.

In further aspects, the present invention relates to an isolated nucleic acid molecule comprising a nucleotide sequence encoding a phenylalanine dehydrogenase polypeptide, or a functional fragment thereof, wherein the encoded polypeptide has at least about 70% sequence identity to a wild-type phenylalanine dehydrogenase enzyme from the organism *Geobacillus thermoglucosidasius*, and wherein the nucleic acid molecule has been optimized for expression in a suitable host cell (e.g., *E. coli*).

In other aspects, the present invention provides use of a phenylalanine dehydrogenase polypeptide, or a functional fragment thereof, for the treatment of hyperphenylalaninemia (e.g., PKU) in a subject, or in the manufacture of a medicament for the treatment of hyperphenylalaninemia, wherein the polypeptide has at least about 70% sequence identity to a wild-type phenylalanine dehydrogenase enzyme from the organism *Geobacillus thermoglucosidasius*.

The compositions and methods described herein allow deliver of PheDH polypeptides that are particularly stable and active under harsh temperature and pH conditions to the intestines of subjects. Accordingly, the compositions and methods of the present invention are useful for reducing phenylalanine levels in the gastrointestinal tract and blood of subjects having disorders characterized by hyperphenylalaninemia, particularly PKU.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example aspects of the invention, as illustrated in the accompanying drawings.

FIG. 2A depicts a $NAD^+$ titration curve, wherein enzyme activity was measured by monitoring NADH formation in the presence of 5 mM of phenylalanine (Phe) while varying $NAD^+$ concentration (0-1.25 mM). FIG. 2B depicts a Phe titration curve using the same conditions as for NAD+ titration but maintaining the NAD$^+$ concentration constant at 1.25 mM, while varying the Phe concentration (0-2.5 mM).

In FIGS. 3D-3G, "E1" represents denatured (heat treated) GtPheDH and "E2" represents non-denatured GtPheDH.

FIG. 5A shows representative sectioning of mouse intestine (top portion of FIG. 5A) and the pH associated with each of the sections (bottom portion of FIG. 5A—yellow=acid; blue=basic). FIG. 5B shows Phe concentrations (µM) across the different regions of the intestine shown in FIG. 5A in comparison to the level found in blood.

FIGS. 8A-8D shows an alignment of the wild-type nucleotide sequence encoding GtPheDH (SEQ ID NO: 2) against a codon-optimized nucleotide sequence encoding GtPheDH (SEQ ID NO: 3).

FIGS. 9A-9C shows the results of PheDH activity assay in different assay buffers: 25 mM, 100 mM, and 200 mM Gly/KOH/KCl, pH 10.4.

DETAILED DESCRIPTION OF THE INVENTION

Figure 1:
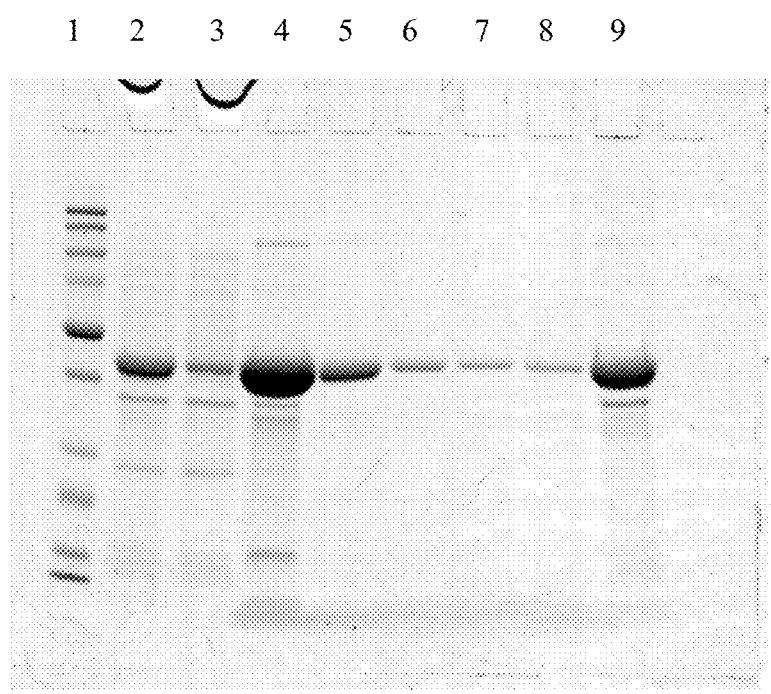
FIG. 1 is an image depicting a polyacrylamide gel electrophoresis of *Geobacillus thermoglucosidasius* PheDH that was expressed in *E. coli* an isolated from inclusion bodies. The gel was stained with coomasie blue. Lane 1: molecular weight marker; lane 2: whole lysate; lane 3: lysate supernatant; lane 4: lysate pellet; lane 5: wash 1 supernatant; lane 6: wash 2 supernatant; lane 7: wash 3 supernatant; lane 8: wash 4 supernatant; lane 9: solubilized enzyme (working product).

A description of example aspects of the invention follows.

PKU is a recessively inherited disease caused by mutations in the gene encoding the enzyme phenylalanine hydroxylase (PAH) and is one of the most common inborn defects in metabolism. The effect of PAH mutations on hepatic enzyme function and the resultant disruption to Phe homeostasis has been described, but the major clinical effect of PKU relates to brain development and cognitive function (Kayaalp, E. et al., *Amer. J. of Human Genetics* 61:1309-1317, 1997). PKU can also result from deficiencies affecting the biosynthetic pathway of tetrahydrobiopterin (BH$_4$), which is required for proper functioning of PAH. Untreated PKU is also associated with growth failure, poor skin pigmentation, microcephaly, seizures, and global developmental delays. Clinically, high blood phenylalanine (Phe) disturbs brain development in childhood and alters brain function at all ages (Hoedt, A. E., et al, *J. of Inherited Metabol. Disease,* 34:165-171, 2011).

The primary therapy for PKU and the associated hyperphenylalaninemia (HPA) involves limiting dietary intake of Phe. This treatment was first administered in 1958 (Woolf, et al., *Arch. of Disease in Childhood* 33:31-45, 1958) and it has been used for the treatment of many cases from classic PKU to mild HPA. Current trends in PKU therapy aim to reduce blood Phe concentrations by either stabilizing the enzyme (BH$_4$ therapy), replacing the enzyme, replacing the defective gene (gene therapy), or blocking the intake of Phe by the brain in an indirect way (large neutral amino acid (LNAA) therapy that blocks the transport of Phe to the brain and blood intake of Phe from the gut) (Williams, R. A. et al., *The Clinical Biochemist Reviews/Australian Assoc. of Clin. Biochemists* 29:31-41, 2008). Each of these therapies has its own limitations; some are effective only in a subset of PKU patients while others require continuous dosage throughout the day.

The present invention provides, in part, a method of treating hyperphenylalaninemia (HPA) (e.g., phenylketonuria—PKU) by administering a phenylalanine dehydrogenase (PheDH) enzyme, which catabolizes phenylalanine, to a subject in need thereof. The PheDH polypeptides described herein are capable of catabolizing Phe in extreme conditions (e.g., low pH, high temperature), making them a useful therapeutic agent for reducing Phe concentrations in the low pH environment of the intestines and, ultimately, the blood. Furthermore, the high stability of the PheDH polypeptides described herein allow for the delivery of the active enzyme to the intestinal tract of the subject. In additional embodiments, the PheDH polypeptides described herein can be delivered to the blood (e.g., by parenteral administration) to reduce Phe levels.

Phenylalanine Dehydrogenase Compositions

Accordingly, the present invention provides, in one aspect, a composition comprising a phenylalanine dehydrogenase (PheDH) protein, or a functional fragment thereof, having at least about 70% sequence identity to the wild-type PheDH enzyme from the organism *Geobacillus thermoglucosidasius* (SEQ ID NO: 1).

Figure 7:
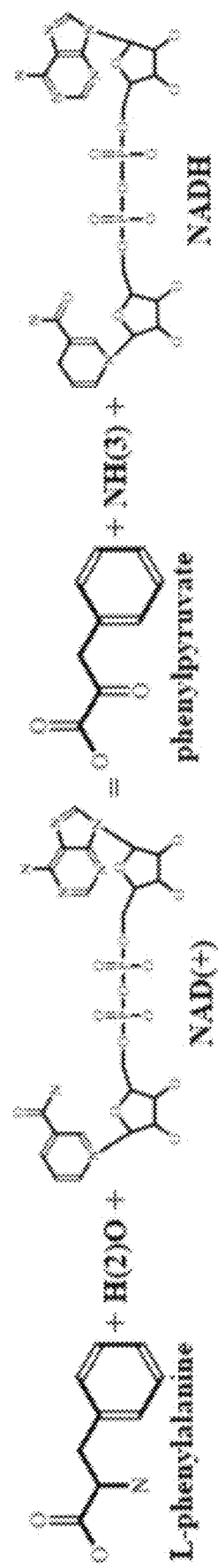
FIG. 7 illustrates the reaction catalyzed by PheDH.

As used herein, the term "phenylalanine dehydrogenase" or "PheDH" refers to any of a class of enzymes (EC 1.4.1.20) that catalyze the conversion of phenylalanine to phenylpyruvate according to the general reaction: L-phenylalanine+H$_2$O+NAD$^+$ ⇌ phenylpyruvate+NH$_3$+NADH+H$^+$. The reaction catalyzed by PheDH is illustrated in FIG. 7. The "EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze. The terms "PheDH" and "phenylalanine dehydrogenase" each encompass full-length phenylalanine dehydrogenase enzymes as well as functional fragments of those enzymes. In one aspect, the PheDH polypeptide is a full-length PheDH enzyme. In another aspect, the PheDH polypeptide is a functional fragment of a full-length PheDH enzyme. The term "functional fragment", refers to a portion of a full-length PheDH enzyme that retains some or all of the activity (e.g., biological activity) of the full-length polypeptide, such as the ability to catalyze the conversion of phenylalanine to phenylpyruvate according to the general reaction: L-phenylalanine+H$_2$O+NAD$^+$ ⇌ phenylpyruvate+NH$_3$+NADH+H$^+$. The functional fragment can be any size, provided that the fragment retains phenylalanine dehydrogenase activity. For example, a functional fragment of a PheDH can be, for example, about 20, 30, 40, 50, 60, 70, 80, 90, 100, 150, 200, 300, 350, etc., amino acids in length.

As used herein, "polypeptide" and "protein" are used interchangeably to denote a polymer of at least two amino acids covalently linked by an amide bond, regardless of length or post-translational modification (e.g., glycosylation or phosphorylation).

In some aspects, the PheDH polypeptide, or functional fragment thereof, has at least about 70% sequence identity to the wild-type *Geobacillus thermoglucosidasius* phenylalanine dehydrogenase (GtPheDH) (SEQ ID NO: 1). For example, the PheDH polypeptide, or functional fragment thereof, can comprise an amino acid sequence having at least about 70%, 75%, 80%, 85%, 86%, 87%, 88%, 89%, 90%, 91%, 92%, 93%, 94%, 95%, 96%, 97%, 98%, 99% or more identity to an amino acid sequence in SEQ ID NO: 1. In one aspect, the PheDH polypeptide, or functional fragment thereof, has 100% identity to an amino acid sequence in SEQ ID NO: 1. PheDH polypeptides, or functional fragments thereof, having at least about 70% or more sequence identity to an amino acid sequence in SEQ ID NO: 1 can differ from SEQ ID NO:1, for example, as a result of one or more substitutions (e.g., conservative substitutions, non-conservative substitutions), deletions, or insertions, or a combination thereof, with respect to the wild-type GtPheDH sequence (SEQ ID NO: 1). In some embodiments, the PheDH polypeptides, or functional fragments thereof, have improved solubility over wild-type PheDH.

In certain embodiments, the PheDH polypeptides, or functional fragments thereof, have improved enzymatic activity (e.g., at low pH), improved protease resistance (e.g., resistance to pepsin, resistance to chymotrypsin), or improved reversible deactivation, or any combination thereof, compared to wild-type PheDH. Examples PheDH polypeptides having at least about 70% or more sequence identity to wild-type GtPheDH that have improved properties/characteristics compared to wild-type GtPheDH include, e.g., PheDH polypeptides comprising SEQ ID NO: 6, SEQ ID NO: 7, SEQ ID NO: 8, SEQ ID NO: 9, SEQ ID NO: 10, or SEQ ID NO: 11 (see Example 6 herein).

As used herein, the term "sequence identity" means that two nucleotide or amino acid sequences, when optimally aligned, such as by the programs GAP or BESTFIT using default gap weights, share at least, e.g., 70% sequence identity, or at least 80% sequence identity, or at least 85% sequence identity, or at least 90% sequence identity, or at least 95% sequence identity or more. For sequence comparison, typically one sequence acts as a reference sequence (e.g., parent sequence), to which test sequences are compared. The sequence identity comparison can be examined throughout the entire length of a given protein, or within a desired fragment of a given protein. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., *Current Protocols in Molecular Biology*). One example of algorithm that is suitable for determining percent sequence identity and sequence similarity is the BLAST algorithm, which is described in Altschul et al., *J. Mol. Biol.* 215:403 (1990). Software for performing BLAST analyses is publicly available through the National Center for Biotechnology Information (publicly accessible through the National Institutes of Health NCBI internet server). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

As used herein, "wild-type" and "naturally-occurring" refer to the canonical nucleotide or amino acid sequence of a PheDH enzyme as found in nature (e.g., as occurs in the bacterium *Geobacillus thermoglucosidasius*).

In some embodiments, PheDH polypeptides or fragments thereof include a tag (e.g., His tag) at the N- and/or C-terminus of the polypeptide. Such tags can be useful, e.g., for protecting the PheDH polypeptide from degradation.

As will be appreciated by those of skill in the art, a PheDH suitable for use in the compositions and methods described herein can be obtained from a variety of sources. For example, a PheDH enzyme can be isolated or purified from a variety of bacterial sources expressing the enzyme. Such bacteria can be natural isolates or genetically-engineered laboratory strains, among others. In a particular example, PheDH is isolated from a thermophilic bacterium, (e.g., *Geobacillus thermoglucosidasius*, strain C56-YS93). PheDH isolated from thermophilic organisms typically exhibit sufficient stability in extreme conditions (e.g., higher temperatures, acidic and/or basic pH), to allow them to function in harsh environments, such as the gut.

In other aspects, the PheDH can be produced recombinantly in a suitable host cell (e.g., bacteria, yeast, insect cells, mammalian cells) according to methods known in the art. See, e.g., *Current Protocols in Molecular Biology*, Second Edition, Ausubel et al. eds., John Wiley & Sons, 1992; and *Molecular Cloning: a Laboratory Manual*, 2nd edition, Sambrook et al., 1989, Cold Spring Harbor Laboratory Press. For example, a nucleic acid molecule comprising a nucleotide sequence encoding a PheDH polypeptide, or functional fragment thereof, can be introduced and expressed in suitable host cells (e.g., commercially available strains such as Rosetta™ 2 cells), and the expressed PheDH polypeptide or functional fragment thereof can be isolated/purified from the host cells (e.g., in inclusion bodies) using routine methods and readily available reagents. As those of skill in the art would appreciate, a given nucleotide sequence encoding a protein e.g., exhibits higher expression and/or better solubility in one host cell as compared to another. For example, codon-optimized sequences described herein are transformed into, e.g., BL21 cells and induced with Rhamnose, for improved PheDH production.

Accordingly, in a further aspect, the present invention also provides an isolated nucleic acid molecule comprising a nucleotide sequence encoding a PheDH polypeptide, or a functional fragment thereof, wherein the encoded polypeptide has at least about 70% sequence identity to a wild-type PheDH enzyme from the organism *Geobacillus thermoglucosidasius*. The term "nucleic acid" is used herein to refer to a polymer comprising multiple nucleotide monomers (e.g., ribonucleotide monomers or deoxyribonucleotide monomers). "Nucleic acid" includes, for example, genomic DNA, cDNA, RNA, and DNA-RNA hybrid molecules. Nucleic acid molecules can be naturally occurring, recombinant, or synthetic. In addition, nucleic acid molecules can be single-stranded, double-stranded or triple-stranded. In some aspects, nucleic acid molecules can be modified. Nucleic acid modifications include, for example, methylation, substitution of one or more of the naturally occurring nucleotides with a nucleotide analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). "Nucleic acid" does not refer to any particular length of polymer and therefore, can be of substantially any length, typically from about six (6) nucleotides to about $10^9$ nucleotides or larger. In the case of a double-stranded polymer, "nucleic acid" can refer to either or both strands of the molecule.

Although the genetic code is degenerate in that most amino acids are represented by several codons (called "synonyms" or "synonymous" codons), it is understood in the art that codon usage by particular organisms is nonrandom and biased towards particular codon triplets. Accordingly, in a particular aspect, the nucleic acid encoding a PheDH polypeptide, or functional fragment thereof, includes a nucleotide sequence that has been optimized for expression in a particular type of host cell (e.g., through codon optimization). Codon optimization refers to a process in which a polynucleotide encoding a protein of interest is modified to replace particular codons in that polynucleotide with codons that encode the same amino acid(s), but are more commonly used/recognized in the host cell in which the nucleic acid is being expressed. In some aspects, the polynucleotides encoding PheDH described herein are codon optimized for expression in *E. coli*. An example of a codon-optimized nucleotide sequence encoding a PheDH is SEQ ID NO: 3. An alignment comparing the codon-optimized nucleotide sequence (SEQ ID NO: 3) against the wild-type nucleotide sequence (SEQ ID NO: 2) is shown in FIG. 8.

In additional aspects, the nucleotide sequence encoding the PheDH polypeptide, or functional fragment thereof, is operably-linked to a heterologous sequence, e.g., for expression in a host cell. As used herein, an amino acid or nucleotide sequence is "heterologous" to another sequence with which it is operably linked if the two sequences are not associated in nature.

In one aspect, the heterologous sequence is a promoter sequence. As used herein, a "promoter sequence" refers to a nucleic acid sequence that is recognized by a host cell for expression of a polynucleotide of interest, such as a coding sequence. The promoter sequence contains transcriptional control sequences that mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell. For bacterial host cells, suitable promoters for directing transcription of the nucleic acid constructs of the present disclosure, include, but are not limited to promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., *Proc. Natl. Acad. Sci. USA* 75: 3727-3731, 1978), as well as the tac promoter (See e.g., DeBoer et al., *Proc. Natl. Acad. Sci. USA* 80: 21-25, 1983). Examples of promoters for filamentous fungal host cells, include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Examples of yeast cell promoters can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., *Yeast* 8:423-488, 1992).

Other heterologous sequences that can be operably linked to a nucleotide sequence encoding a PheDH include, but are not limited to, fusion moieties (e.g., maltose binding protein (MBP), glutathione-S-transferase (GST)), signal peptide sequences, propeptide sequences, initiation sequences, terminator sequences, transcriptional and translational stop signals, and selectable marker sequences. In some embodiments, heterologous nucleotide sequences can encode a fusion moiety such as a tag, e.g., Histidine-tag, Myc tag, hemagglutinin (HA) tag. Other suitable heterologous sequences that can be adapted to various methods of protein expression are readily available and known in the art.

"Operably linked" is defined herein as a configuration in which a heterologous sequence is appropriately placed (e.g., in a functional relationship) at a position relative to a polynucleotide of interest such that the heterologous sequence, e.g., directs or regulates the expression of the polynucleotide encoding a polypeptide of interest, or is expressed in-frame relative to the expression product of the polynucleotide of interest.

In some aspects, the present invention also provides a plasmid comprising the isolated nucleic acid molecule described herein. Generally, the term "plasmid" is used interchangeably with the term "vector", and refers to a nucleic acid construct for introducing a nucleic acid sequence into a cell. In some aspects, the plasmid is an expression plasmid that is operably linked to a suitable heterologous sequence capable of effecting the expression in a suitable host of the polypeptide encoded by the nucleic acid sequence, as described herein.

As used herein, the term "host cell" refers to a suitable host for expressing a nucleic acid encoding a PheDH enzyme. In some aspects, the host cells are prokaryotic or eukaryotic cells that have been transformed or transfected with vectors constructed using recombinant DNA techniques known in the art. Examples of suitable host cells include various species of yeast (e.g., *Pichia pastoris* and *Saccharomyces cerevisiae*), various lines of insect cells, various lines of mammalian cells (e.g., CHO cells), and various species of bacteria cells (e.g. *E. coli* and *B. subtilis*). In certain aspects, the present invention provides a host cell comprising a nucleic acid encoding a PheDH polypeptide described herein. In a particular aspect, the host cell is *E. coli*.

Using known methods and reagents, including, e.g., lysozyme treatment, sonication, filtration, salting-out, ultra-centrifugation, and chromatography, a recombinantly-expressed PheDH can be recovered from host cells and/or the host cell culture medium.

Pharmaceutical Formulations Comprising PheDH

The present invention also provides pharmaceutical formulations comprising a PheDH polypeptide, or a functional fragment thereof, and a pharmaceutically-acceptable carrier. The pharmaceutical formulations described herein are suitable for use in decreasing the concentration of phenylalanine in a subject in need thereof (e.g., in the intestines, blood, or both of a subject).

In a particular aspect, the present invention provides a pharmaceutical formulation comprising a PheDH polypeptide, or a functional fragment thereof, wherein the polypeptide has at least about 70% sequence identity to a wild-type PheDH enzyme from the organism *Geobacillus thermoglucosidasius*, and a pharmaceutically-acceptable carrier. In one aspect, the wild-type PheDH polypeptide comprises the amino acid sequence set forth in SEQ ID NO: 1. In a particular aspect, the PheDH polypeptide in the formulation has at least about 95% sequence identity to SEQ ID NO: 1.

The pharmaceutical formulations described herein comprise a therapeutically effective amount of a PheDH described herein and one or more pharmaceutically acceptable excipients, vehicles diluents, stabilizers, preservatives, solubilizers, emulsifiers, adjuvants and/or carriers. For example, such pharmaceutical compositions can include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol); see, e.g., *Remington's Pharmaceutical Sciences*, 18th Edition (1990, Mack Publishing Co., Easton, Pa.) pages 1435:1712, which are herein incorporated by reference.

Depending on the intended mode of administration, the pharmaceutical formulations can be in a solid, semi-solid, or liquid dosage form, such as, for example, tablets, suppositories, pills, capsules, microspheres, powders, liquids, suspensions, creams, ointments, lotions or the like, possibly contained within an artificial membrane, preferably in unit dosage form suitable for single administration of a precise dosage.

For example, suitable doses per single administration of PheDH include, e.g., doses of about or greater than about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 20 mg, about 30 mg, about 40 mg, about 50 mg, about 100 mg, about 200 mg, about 300 mg, about 400 mg, about 500 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, or about 3,000 mg. Each dose can be administered over a period of time deemed appropriate by a skilled practitioner.

In general, the PheDH can be administered in a pharmaceutical formulation, including those suitable for oral (including buccal and sub-lingual), or parenteral (including intramuscular, intraarterial, intrathecal, subcutaneous and intravenous) administration or in a form suitable for administration by inhalation or insufflation. In a particular aspect, the manner of administration is oral, using a convenient single dosage regimen (e.g., daily), which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can be prepared, for example, by dissolving, dispersing, etc., an active compound or conjugate as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in the relevant art (see, e.g., *Remington's Pharmaceutical Sciences*, referenced herein).

For oral administration, the formulation will generally take the form of a tablet, capsule, or softgel capsule, or may be an aqueous or nonaqueous liquid solution, suspension (e.g., microsphere suspension), or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions (e.g., microsphere suspensions) are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like. In other aspects, the formulation can take the form of a powder that can be dissolved into an aqueous solution for administration. The aqueous or nonaqueous liquid solution can also be added to an aqueous solution for administration (e.g., liquid solution can be mixed with baby formula).

In a particular aspect, the oral formulation (e.g., tablet, capsule, buffered solutions, or suspensions) comprises polymers that are resistant to degradation by digestive enzymes and/or pH (e.g., an acidic pH). For example, the active ingredient can be embedded in a polymer, or the tablet or capsule can be coated with a polymer that is resistant to degradation by digestive enzymes (e.g., in the stomach). Various polymers that are resistant to digestive enzymes are known in the art. For example, the tablet or capsule can be coated with polymers such as EUDRAGIT® (L or S formulations) to protect the enzyme from the stomach and intestinal environments, thereby stabilizing the enzyme (e.g., prevents degradation or inactivation, or both, of the enzyme) in the gastrointestinal tract of the subject. Other methods of designing oral formulations to protect an active ingredient from the gastrointestinal environment are known in the art (see, e.g., Muheem et al., Saudi Pharmaceutical Journal (2014), http://dx.doi.org/10.1016/j.jsps.2014.06.004, for a review on the strategies for oral delivery of proteins). Such formulation methods include, e.g., packaging into microspheres or nanoparticles, and use of mucoadhesives.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained. For example, the parenteral formulation can be designed such that the enzyme is released as a function of the pH of the intestinal tract.

In some aspects, the pharmaceutical formulation further comprises an additional therapeutic agent. In certain aspects, the additional therapeutic agent is a cofactor that is required for PheDH activity. For example, as described herein, nicotinamide adenine dinucleotide ($NAD^+$) can be included in the pharmaceutical formulation along with PheDH in a suitable ratio. In other aspects, the additional therapeutic can be included to supplement PheDH activity. Such additional therapeutics include, e.g., a phenylalanine ammonia lyase (PAL) enzyme or a derivative thereof, such as a pegylated PAL (see, e.g., U.S. Application Nos. 2014/0314843, 2008/0008695, 2013/0039898, the entire contents of which are incorporated by reference herein), as well as 5,6,7,8-tetrahydrobiopterin ($BH_4$) and large neutral amino acid (LNAA) therapy.

Methods of Treating Hyperphenylalaninemia (HPA)

The compositions and formulations described herein are useful for decreasing phenylalanine (Phe) levels in a subject (e.g., in the intestines and/or blood of the subject). Thus, in one aspect, the present invention provides a method of reducing the level of Phe in a subject in need thereof, comprising administering to the subject an effective amount of a PheDH polypeptide, or a functional fragment thereof, wherein the polypeptide has at least about 70% sequence identity to a wild-type phenylalanine dehydrogenase enzyme from the organism *Geobacillus thermoglucosidasius*. In one aspect, the PheDH polypeptide has at least about 70% sequence identity to SEQ ID NO: 1. In another aspect, the PheDH polypeptide has at least about 95% sequence identity to SEQ ID NO: 1. In particular aspects, the phenylalanine dehydrogenase polypeptide having at least about 70% sequence identity to SEQ ID NO: 1 comprises an amino acid sequence selected from the group consisting of SEQ ID NO: 6, SEQ ID NO: 7, SEQ ID NO: 8, SEQ ID NO: 9, SEQ ID NO:10, and SEQ ID NO:11.

An "effective amount" of active ingredient (e.g., PheDH) is a therapeutically, prophylactically, or diagnostically effective amount, which can be readily determined by a person skilled in the art by taking into consideration such factors as body weight, age, and therapeutic goal. In particular, as it relates to PheDH, an effective amount refers to an amount which results in a decrease in intestinal and/or serum Phe concentrations that provides a benefit (e.g., therapeutic benefit) to a subject. In certain aspects, an effective amount of PheDH is an amount that decreases serum Phe to a concentration below 360 μmol/L (e.g., for adults), however, the effective amount will vary from one subject to another depending upon a number of factors, including age and the overall physical condition of the subject. For example, in a pediatric subject, an effective amount of PheDH is an amount that decreases serum Phe to a concentration below about 120 μmol/L. A target for blood (e.g., plasma, serum, whole blood) phenylalanine levels would be 400 μmol/L or less; however any reduction in baseline elevated phenylalanine level for a PKU patient will provide benefit in neuroprotection. The effective amount of PheDH used for therapy gives an acceptable rate of Phe decrease (in the intestines and/or serum) and maintains this value at a beneficial level (usually a decrease of at least about 30% and typically in a range of 10% to 90%), or maintains a stable phenylalanine level with an increase in dietary whole protein containing phenylalanine. A therapeutically effective amount of a PheDH composition described herein can be readily ascertained by one skilled in the art (e.g., a skilled medical professional).

As used herein, the term "subject" encompasses mammals such as humans, non-human primates, livestock, companion animals, and laboratory animals (e.g., rodents and lagamorphs). In a particular aspect, the subject is a human.

As used herein, the term "subject in need thereof" or "patient" refers to a subject whose Phe concentration in the blood is above a desirable level, as determined by a skilled medical professional.

In some aspects, a subject in need thereof has hyperphenylalaninemia (HPA). Thus, in certain aspects, the present methods are directed to methods for treating a subject that has HPA. The present methods are useful for the treatment of a variety of conditions associated with HPA. For example, the PheDH compositions and formulations described herein can be used to treat patients with mild HPA, patients with moderate PKU, patients with severe ("classic") PKU, patients with malignant PKU, patients with co-factor non-responsive PKU, and any subpopulation thereof. In other examples, the PheDH compositions and formulations described herein can also be used to treat patients with HPA as a result of a $BH_4$ deficiency. The varieties of mild, moderate, and severe forms of HPA condition are known in the art and can be readily diagnosed by a skilled medical professional (e.g., a physician). Examples of patients that are amenable to treatment with PheDH compositions described herein include pregnant women and infants with serum concentrations of more than 200 μM of Phe.

In certain aspects, the PheDH is administered orally and the PheDH is delivered to the intestinal tract of the subject. Formulations suitable for oral delivery of the enzyme include any of the oral formulations described herein, among others.

In some aspects, the present methods further comprise administering an additional therapeutic agent or treatment to the subject in combination with a PheDH described herein. The additional therapeutic agent can be administered before, simultaneously with, or after the administration of a formulation comprising PheDH. Accordingly, PheDH and an additional therapeutic agent can be administered together in a single formulation (e.g., a tablet, capsule, powder, injectable liquid, etc.), or can be administered in separate formulations, e.g., either simultaneously or sequentially, or both.

The duration of time between the administration of PheDH and one or more additional therapeutic agents will depend on the nature of the therapeutic agent(s). In addition, the PheDH and the additional therapeutic agent(s) may or may not be administered on similar dosing schedules. For example, the PheDH and the additional therapeutic agent may have different half-lives and/or act on different timescales such that the PheDH is administered with greater frequency than the additional therapeutic agent, or vice-versa. The number of days in between administration of therapeutic agents can be appropriately determined by persons of ordinary skill in the art according to the safety and pharmacodynamics of each drug.

In one aspect, the additional therapeutic agent is a cofactor that is required for PheDH activity. For example, as described herein, nicotinamide adenine dinucleotide ($NAD^+$) can be included into the pharmaceutical formulation along with PheDH in a suitable ratio, as a single dosage form. Alternatively, $NAD^+$ can be administered separately, as described above. In other aspects, the additional therapeutic agent is, e.g., a phenylalanine ammonia lyase (PAL), or a derivative thereof (e.g., pegylated PAL), $BH_4$, or a large neutral amino acid (LNAA).

In some aspects, the PheDH compositions and formulations described herein can be used in conjunction with a protein-restricted diet.

In certain aspects, the methods described herein further comprise determining the concentration of phenylalanine in a sample from the subject (e.g., a blood sample or a urine sample) following administration of the PheDH polypeptide, or functional fragment thereof (e.g., to monitor efficacy of the PheDH).

In one aspect, the concentration of Phe is determined in a blood sample. A variety of methods are available for determining the presence of Phe in blood (see, e.g., Shaw et al., *Analytical Methods in Phenylketonuria-Clinical Biochemistry*, In Bickett et al. Eds., *Phenylketonuria and Some Other Inborn Errors of Amino Acid Metabolism*, Stuttgart, Georg Thiem Verlag, 47-56 (1971)). Typically, phenylalanine concentrations are determined from the serum of a patient using a fluorometric assay. This assay relies on the formation of fluorescent substance when phenylalanine is heated with ninhydrin in the presence of leucylalanine (McCaman, et al., J. Lab. Clin. Med. 59:885-890 (1962)).

A common method for determining Phe concentrations is the Guthrie test in which discs are punctured from filter paper that has been saturated with a blood sample from the patient. The uniform discs are incubated in a tray of agar that has been seeded with *Bacillus subtilis* and contains a specific inhibitor of *Bacillus subtilis* growth. As the phenylalanine transfers from the uniform discs onto the agar, the Phe reverse the inhibition of bacterial growth thereby yielding an area of bacterial growth that can be correlated to phenylalanine concentration by comparison to similar assays performed using discs containing known amounts of Phe.

Other methods of quantifying Phe concentration include HPLC, mass spectrometry, thin layer chromatography and the like. Further, devices for detecting Phe levels are described in, e.g., WO2014062985 A1, the contents of which are incorporated by reference herein in their entirety. Such methods can be used to determine the plasma Phe concentration of a patient before the therapy and to monitor the Phe concentration during the therapeutic regimen to determine the efficacy.

Plasma Phe levels of the patients can be monitored at convenient intervals (e.g., daily, every other day or weekly) throughout the time course of the therapeutic regimen. By monitoring the plasma Phe levels with such regularity, the efficacy of the treatment can be assessed, allowing for adjustments to the amount of PheDH administered to the subject, and/or dietary protein requirements accordingly.

In various aspects, the present invention also provides the use of a PheDH polypeptide, or a functional fragment thereof, in the treatment of hyperphenylalaninemia in a subject in need thereof, wherein the polypeptide has at least about 70% sequence identity to a wild-type phenylalanine dehydrogenase enzyme from the organism *Geobacillus thermoglucosidasius*. In certain aspects, the HPA is moderate PKU, or severe ("classic") PKU. In other aspects, the polypeptide has at least about 70% sequence identity to SEQ ID NO: 1. In further aspects, the polypeptide has at least about 95% sequence identity to SEQ ID NO: 1. In particular aspects, the polypeptide comprises an amino acid sequence selected from the group consisting of SEQ ID NO: 6, SEQ ID NO: 7, SEQ ID NO: 8, SEQ ID NO: 9, SEQ ID NO: 10, and SEQ ID NO: 11.

In further aspects, the present invention provides the use of a PheDH polypeptide, or a functional fragment thereof, in the manufacture of a medicament for the treatment of hyperphenylalaninemia in a subject, wherein the polypeptide has at least about 70% sequence identity to a wild-type phenylalanine dehydrogenase enzyme from the organism *Geobacillus thermoglucosidasius*. In certain aspects, the HPA is moderate PKU, or severe ("classic") PKU. In other aspects, the polypeptide has at least about 70% sequence identity to SEQ ID NO: 1. In further aspects, the polypeptide has at least about 95% sequence identity to SEQ ID NO: 1.

GtPheDH Antibody Compositions

The present invention also provides isolated antibodies and fragments thereof that bind to GtPheDH polypeptides, in particular, to a GtPheDH polypeptide comprising an amino acid sequence selected from the group consisting of SEQ ID NO: 1, SEQ ID NO: 6, SEQ ID NO: 7, SEQ ID NO: 8, SEQ ID NO: 9, SEQ ID NO: 10, and SEQ ID NO: 11, among others. The antibody compositions used herein are suitable for use in detecting GtPheDH (e.g., for research or diagnostic purposes) or for isolating GtPheDH. In some embodiments, the antibody compositions disclosed herein can act as an antagonist to inhibit GtPheDH activity, or as an agonist to enhance GtPheDH activity.

As used herein, "isolated antibody" means an antibody that is substantially free of its natural environment. For instance, an isolated antibody or nucleic acid is substantially free of cellular material and other proteins from the cell or tissue source from which it is derived. The term "isolated" also refers to preparations where the isolated antibody is sufficiently pure to be administered as a pharmaceutical composition, or at least 70-80% (w/w) pure, at least 80-90% (w/w) pure, 90-95% pure; and, at least 95%, 96%, 97%, 98%, 99%, or 100% (w/w) pure.

The antibodies disclosed herein comprise: (a) an immunoglobulin heavy chain variable region comprising the structure $CDR_{H1}$-$CDR_{H2}$-$CDR_{H3}$, and (b) an immunoglobulin light chain variable region comprising the structure $CDR_{L1}$-$CDR_{L2}$-$CDR_{L3}$, wherein the heavy chain variable region and the light chain variable region together define a single binding site for binding GtPheDH enzyme.

In some embodiments, the antibody binds specifically to a GtPheDH polypeptide comprising an amino acid sequence selected from the group consisting of SEQ ID NO: 1, SEQ ID NO: 6, SEQ ID NO: 7, SEQ ID NO: 8, SEQ ID NO: 9, SEQ ID NO: 10, and SEQ ID NO: 11, with negligible binding to other proteins present in the sample.

The present invention also provides isolated nucleic acids comprising a nucleotide sequence encoding a HCVR and/or a LCVR of an antibody disclosed herein, or a fragment thereof. A nucleic acid according to the present invention can comprise DNA or RNA, and can be wholly or partially synthetic. For example, DNA molecules encoding an HCVR and/or LCVR of an antibody disclosed herein can be chemically synthesized. Synthetic DNA molecules can be ligated to other appropriate nucleotide sequences, including, e.g., constant region coding sequences, and expression control sequences, to produce conventional gene expression constructs encoding the desired antibodies. Production of defined gene constructs is within routine skill in the art. Alternatively, nucleotide sequences can be cloned out of hybridomas, for example, by conventional hybridization techniques or polymerase chain reaction (PCR) techniques, using synthetic nucleic acid probes whose sequences are based on sequence information provided herein.

Techniques and protocols for engineering and production of nucleic acids are known in the art. See, e.g., *Current Protocols in Molecular Biology*, Second Edition, Ausubel et al. eds., John Wiley & Sons, 1992.

Methods of producing an HCVR and/or LCVR, or a fragment thereof, of an antibody disclosed herein are within the scope of the invention. The method comprises: (a) growing a host cell containing an expression vector encoding the HCVR and/or LCVR under conditions so that the host cell expresses the antibody comprising the HCVR and/or LCVR, or a fragment thereof; and (b) isolating the antibody comprising the HCVR and/or LCVR, or a fragment thereof.

Suitable conditions for antibody expression and isolation or purification depend on the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence. The expressed secreted protein accumulates in refractile or inclusion bodies, and can be harvested after disruption of the cells by French press or sonication. The refractile bodies then are solubilized, and the proteins refolded and cleaved by methods known in the art.

If the engineered gene is to be expressed in eukaryotic host cells, e.g., CHO (Chinese hamster ovary) cells, it is first inserted into an expression vector containing a suitable eukaryotic promoter, a secretion signal, a poly A sequence, and a stop codon. Optionally, the vector or gene construct contains enhancers and introns. This expression vector optionally contains sequences encoding all or part of a constant region, enabling an entire, or a part of, a heavy or light chain to be expressed. The gene construct can be introduced into eukaryotic host cells using conventional techniques. The host cells express VL or VH fragments, VL-VH heterodimers, VH-VL or VL-VH single chain polypeptides, complete heavy or light immunoglobulin chains, or portions thereof, each of which may be attached to a moiety having another function.

In some embodiments, a host cell is transfected with a single vector expressing a polypeptide expressing an entire, or part of, a heavy chain (e.g., a heavy chain variable region) or a light chain (e.g., a light chain variable region). In some embodiments, a host cell is transfected with a single vector encoding (a) a polypeptide comprising a heavy chain variable region and a polypeptide comprising a light chain variable region, or (b) an entire immunoglobulin heavy chain and an entire immunoglobulin light chain. In some embodiments, a host cell is co-transfected with more than one expression vector (e.g., one expression vector expressing a polypeptide comprising an entire, or part of, a heavy chain or heavy chain variable region, and another expression vector expressing a polypeptide comprising an entire, or part of, a light chain or light chain variable region).

A polypeptide comprising an immunoglobulin heavy chain variable region or light chain variable region can be produced, for example, by growing (culturing) a host cell transfected with an expression vector encoding such a variable region, under conditions that permit expression of the polypeptide. Following expression, the polypeptide can be harvested and purified or isolated using techniques known in the art, e.g., affinity tags such as glutathione-S-transferase (GST) or histidine tags.

The antibodies of the present invention can be produced, e.g., by growing (culturing) a host cell transfected with, for example: (a) an expression vector that encodes a complete or partial immunoglobulin heavy chain, and a separate expression vector that encodes a complete or partial immunoglobulin light chain; or (b) a single expression vector that encodes both chains (e.g., complete or partial heavy and light chains), under conditions that permit expression of both chains. The intact antibody (or antigen-binding fragment) can be harvested and purified or isolated using techniques known in the art, e.g., Protein A, Protein G, affinity tags such as glutathione-S-transferase (GST) or histidine tags. It is within ordinary skill in the art to express the heavy chain and the light chain from a single expression vector or from two separate expression vectors.

Wild-type and Variant GtPheDH Amino Acid and Nucleotide Sequences

GtPheDH Amino Acid Sequence
(SEQ ID NO: 1)
MNTVTNQWKAVDIFTQIRDHEQVVFCNDKNTGLKAIIAIHDTTLGPALGG CRMYPYATVEDALFDVLRLSKGMTYKCLAADVDFGGGKAVI<u>IGDPHKDKT</u>

<u>PELFRA</u>FGQFVESLNGRFYTGTDMGTTPDDFVHAMKETNCIVGVPEEYGG

SGDSSVPTALGVIYGIQATNKVIWGSDELHGKTYAIQGLGKVGRKVAERL

LKEGADLYVCDIHPTAIEAIVSYAKKLGANVKVVQGTEIYRTDADIFVPC

AFGNVVNDNTIHVLKVKAIVGSANNQLLDVRHGQLLKEKGILYAPDYIVN

AGGLIQVADELYGLNKERVLQKTKAIYSTLLHIYSRAEADHITTIEAANR

FCEERLQQR<u>SRRNDFFTHRKOPKWDIRR</u>

Underlined regions were used for development of a polyclonal antibody; the entire protein was used to generate monoclonal antibodies.

GtPheDH Nucleotide Sequence
(SEQ ID NO: 2)
ATGAATACCGTTACCAATCAGTGGAAAGCGGTGGATATATTTACGCAAAT

TCGTGACCATGAGCAAGTCGTATTTTGTAATGATAAAAACACGGGATTAA

AAGCAATTATCGCCATTCATGACACAACGTTAGGCCCAGCGCTTGGCGGA

TGTCGGATGTACCCATATGCGACCGTTGAAGACGCACTATTTGATGTGCT

CCGTCTTTCGAAAGGGATGACGTATAAATGCCTTGCGGCAGATGTAGATT

TTGGCGGCGGCAAAGCGGTTATTATCGGAGACCCGCACAAAGACAAGACA

CCGGAATTGTTCCGTGCATTTGGCCAGTTTGTTGAATCGTTGAATGGCCG

GTTTTACACAGGTACTGATATGGGAACGACGCCGGATGATTTCGTTCACG

```
CGATGAAAGAAACAAACTGCATCGTAGGTGTTCCTGAAGAGTATGGCGGC
AGCGGCGATTCTTCAGTACCGACCGCGTTAGGTGTCATTTACGGTATTCA
AGCTACCAATAAAGTGATTTGGGGAAGCGACGAGCTTCATGGAAAAACGT
ACGCCATCCAAGGGTTAGGAAAAGTAGGAAGAAAAGTAGCGGAGCGTTTA
TTGAAAGAAGGAGCGGACTTGTATGTGTGCGATATTCATCCAACGGCAAT
TGAAGCGATTGTATCATATGCAAAAAATTGGGAGCGAACGTAAAAGTTG
TACAAGGGACGGAAATTTACAGAACAGACGCGGATATATTTGTTCCATGT
GCGTTCGGCAATGTTGTAAATGATAATACGATACATGTGTTGAAAGTAAA
AGCGATTGTCGGTTCCGCCAACAATCAATTACTTGATGTGCGCCACGGAC
AGCTGCTGAAAGAGAAAGGAATTTTATACGCGCCAGATTACATCGTTAAC
GCTGGAGGACTTATTCAAGTAGCTGATGAGCTGTACGGATTGAATAAAGA
ACGTGTACTACAAAAAACAAAAGCGATTTATTCGACGCTCCTTCATATTT
ATTCCCGTGCAGAAGCAGACCATATCACAACAATCGAAGCAGCAAACCGT
TTTTGTGAAGAGCGGTTGCAGCAGCGTAGCCGCCGCAATGATTTTTTTAC
GCACCGCAAACAGCCGAAGTGGGATATCCGCCGGTAA
```

GtPheDH Codon-Optimized Nucleotide Sequence
(SEQ ID NO: 3)
```
ATGAATACTGTGACGAATCAATGGAAAGCTGTCGATATCTTTACGCAGAT
CCGCGATCATGAACAAGTTGTTTTCTGTAATGATAAGAACACCGGTCTGA
AGGCTATCATCGCGATTCACGACACCACCCTGGGTCCTGCTCTGGGCGGC
TGCCGTATGTACCCGTACGCGACGGTCGAAGATGCCCTGTTCGATGTCCT
GCGCCTGAGCAAGGGCATGACCTACAAGTGTTTGGCAGCTGATGTAGACT
TTGGTGGCGGCAAAGCCGTGATTATCGGCGATCCGCATAAAGATAAGACC
CCAGAGCTGTTCCGTGCATTTGGTCAGTTTGTGGAGAGCCTCAACGGTCG
TTTCTATACGGGTACCGATATGGGTACCACCCCGGACGACTTCGTGCACG
CGATGAAAGAAACGAACTGCATTGTGGGCGTCCCGGAAGAGTATGGTGGC
TCGGGTGACTCCAGCGTCCCGACCGCATTGGGCGTGATCTACGGCATTCA
AGCGACCAATAAAGTTATCTGGGGTAGCGACGAACTGCACGGTAAGACTT
ACGCAATCCAGGGTCTGGGTAAGGTTGGTCGTAAAGTCGCAGAGCGCCTG
TTGAAAGAGGGTGCGGACCTGTATGTTTGTGATATTCACCCGACGGCGAT
TGAAGCGATCGTGAGCTATGCGAAGAAACTGGGTGCGAATGTCAAAGTCG
TTCAGGGTACGGAAATCTATCGCACCGACGCGGACATTTTCGTGCCGTGC
GCGTTCGGCAATGTTGTCAACGATAACACTATTCATGTTCTGAAAGTTAA
GGCAATCGTTGGTAGCGCGAATAACCAGCTGCTGGACGTGCGTCACGGTC
AACTGCTGAAAGAAAGGGCATCCTGTATGCCCCGGATTACATTGTGAAC
GCCGGTGGCCTGATCCAAGTCGCGGACGAATTATACGGTCTGAACAAAGA
GCGCGTTTTGCAAAAGACCAAGGCAATCTACAGCACCCTGCTGCACATCT
ACTCTCGTGCCGAGGCAGACCATATTACCACCATTGAAGCCGCGAACCGT
TTTTGCGAGGAACGCCTGCAGCAACGCAGCAGACGTAATGACTTTTTCAC
GCACCGTAAACAGCCGAAATGGGATATTCGTCGTTAA
```

GtPheDH Variant 1 (V1) Amino Acid Sequence
(SEQ ID NO: 6)
MNTVTNEWKSADLFTQMREHEQVVFCNDEKTGLKAIIAIHNTTLGPALGG
CRMQPYPTVEAALFDVLRLSKGMTYKCIAADVDFGGGICAVIIGDPRICD
KSPELFRAFGQFVESLNGRFYTGTDMGTTPEDFVHAMKETNCIVGVPQEY
GGSGDSSVPTALGVIYGLQATNKALWGSDDLQGKTYAIQGLGKVGYKVAE
QLLEKGANLYVCDINQAAVDSIVSYAKEIGGSVKVVDGDEIYRTDADVFV
PCAFGNVVNDDTIDLFKVKAIVGSANNQLLDVRHGQMLQERGILYAPDYI
VNAGGLIQVSDELYGPNICERVLQKTICALYSTLLDIYTQAENEQLTTIE
AANRFCENRLEMRSRRNNFFSHICKRPKWDIRL GtPheDH Variant 2 (V2) Amino Acid Sequence
(SEQ ID NO: 7)
MNTVTNEWKSADLFTQMREHEQVVFCNDEKTGLICAIIAIHNTTLGPALG
GCRMQPYPTVEAALFDVLRLSKGMTYKCIAADVDFGGGICAVIIGDPRIC
DKSPELFRAFGQFVESLNGRFYTGTDMGTTPEDFVHAMKETNCIVGVPQE
YGGSGDSSVPTALGVIYGLQATNICALWGSDDLQGKTYAIQGLGKVGYKV
AEQLLEKGADLYVCDINQAAVDSIVSYAICEIGGSVKVVDGDEIYRTDAD
VFVPCAFGNVVNDDTIDLFKVKAIVGSANNQLLDVICHGQMLQEKGILYA
PDYIVNAGGLIQVSDELYGPNICERVLQKTKAIYSTLLDIYTQAENEQLT
TIEAANRECENRLEMRSRRNNFFSHKKRPKWDIRL GtPheDH Variant 3 (V3) Amino Acid Sequence
(SEQ ID NO: 8)
MNTVTNEWKSADLFTQMREHEQVVECNDEKTGLKAIIAIHNTTLGPALGG
CRMQPYPTVEAALFDVLRLSKGMTYKCIAADVDEGGGKAVIIGDPRKDKS
PELFRAFGQFVESLNGRFYTGTDMGTTPEDFVHAMKETNCIVGVPQEYGG
SGDSSVPTALGVIYGLQATNKALWGSDDLQGKTYAIQGLGKVGYKVAEQL
LEKGANLYVCDINQAAVDAIVSYAKEIGGSVKVVDGDEIYRTDADVFVPC
AFGNVVNDDTIDLLKVKAIVGSANNQLLDVRHGQMLQERGILYAPDYIVN
AGGLIQVSDELYGPNICERVLQKTICALYSTLLDIYAQAENEQLTTIEAA
NRECENRLEMRSRRNNFFSHKKRPKWDIRL GtPheDH Variant 4 (V4) Amino Acid Sequence
(SEQ ID NO: 9)
MNTVTNEWKSADLFTQMREHEQVVECNDEKTGLKAIIAIHSTTLGPALGG
CRMQPYPTVEAALFDVLRLSKGMTYKCIAADVDEGGGKAVIIGDPRICDK
SPELFRAFGQFVESLNGRFYTGTDMGTTPEDFVHAMICETNCIVGVPQEY
GGSGDSSVPTALGVIYGLQATNKALWGSDDLQGKTYAIQGLGKVGYKVAE
QLLEKGANLYVCDINQAAVDAIVSYAKEIGGSVKVVDGDEIYSTDADVFV
PCAFGNVVNDDTIDLLKVKAIVGSANNQLLDVRHGQMLQERGILYAPDYI
VNAGGLIQVSDELYGPNKERVLQKTKAIYSTLQNIYAQAENEQLTTIEAA
NRECENRLEARSRRNNFFSHICICRPKWDIRL GtPheDH Variant 5 (V5) Amino Acid Sequence
(SEQ ID NO: 10)
MNTVTNEWKSADLFTQMREHEQVVECNDEATGLKAIIAIHSTTLGPALGG
CRMQPYPTVEAALFDVLRLSKGMTYKCIAADVDEGGGKAVIIGDPRICDK
SPELFRAFGQFVESLNGRFYTGTDMGTTPEDFVHAMKETNCIVGVPQEYG -continued
GSGDSSIPTALGVIYGLQATNKALWGSDDLQGKTYAIQGLGKVGYKVAEQ

LLEKGANLYVCDINQAAVDAIVSYAKEIGGSVKVVDGDEIYSTDADVEVP

CAFGNVVNDDTIDLLKVKAIVGSANNQLLDVRHGQMLQERGILYAPDYIV

NAGGLIQVSDELYGPNKERVLQKTKAIYSTLQNIYAQAENEQLTTIEAAN

QFCENRLEARSRRNNFFSHKKRPKWDIRL

GtPheDH Variant 6 (V6) Amino Acid Sequence
(SEQ ID NO: 11)
MNTVTNEWKSADLFTQMREHEQVVECNDEKTGLKAIIAIFISTTLGPALG

GCRMQPYPTVEAALFDVLRLSKGMTYKCIAADVDEGGGKAVIIGDPRKDK

SPELFRAFGQFVESLNGRFYTGTDMGTTPEDFVHAMKETNCIVGVPQEYG

GSGDSSVPTALGVIYGLQATNICALWGSDDLQGKTYAIQGLGKVGAKVAE

QLLEKGANLYVCDINQAAVDAIVSYAKEIGGSIKVVDGDEIYSTDADVFV

PCAFGNVVNDDTIDLLKVKAIVGSANNQLLDVRHGQMLQERGILYAPDYI

VNAGGLIQVSDELYGPNKERVLQKTKAIYSTLQNIYAQAENEQLTTIEAA

NQFCENRLEARSRRNNFFSHKKRPKWDIRL

As used herein, the singular "a", "an", and "the" include the plural references, unless the context clearly indicates otherwise.

EXEMPLIFICATION

Example 1. Cloning, Expression, and Purification of GtPheDH

Materials and Methods
Cloning
DNA from *Geobacillus thermoglucosidasius* was isolated and the PheDH gene was amplified by PCR using the following primers:

```
Forward:
                                        (SEQ ID NO: 4)
5'-TGTGCTAGCATGAATACCGTTACCAATCAGTGGAAAGC-3';

Reverse:
                                        (SEQ ID NO: 5)
5'-CTCGAGTCATTACCGGCGGATATCCCACTTCG-3'.
```

The forward primer introduces a NheI restriction site and the reverse primer introduces two extra STOP codons along with a XhoI restriction site. Amplification product size was determined by agarose gel electrophoresis. PCR product was purified directly from the PCR reaction mixture using the QIAquick® Gel Extraction kit (Qiagen) and subsequently used for subcloning into pCR-BluntII TOPO® vector using the Zero Blunt® PCR cloning kit (Invitrogen). Subcloning reaction was used to transform One Shot® TOP10 chemically competent cells (Invitrogen) and positive colonies were selected by resistance to the antibiotic kanamycin.

The plasmids present in the kanamycin resistant colonies were isolated using the QIAprep® Spin Miniprep kit (Qiagen) and screened for the presence of the insert in the plasmid by restriction enzymes NheI and XhoI (New England Biolabs). Positive colonies were identified by the presence of a band corresponding to the PCR product size after digestion with the restriction enzymes. One positive colony was selected for isolation of a larger amount of plasmid DNA using the HiSpeed® Plasmid Midi kit (Qiagen). For cloning of the desired gene, destination vectors (expression vectors) pET24 and pET28 (Novagen) were digested at the same time as the selected positive plasmid with the restriction enzymes NheI and XhoI and the digested fragments to be used were isolated from the agarose gel in which they were separated. For cloning of the gene into the expression vectors a ratio 1:3 vector to insert was used for the ligation reaction. Once the ligation reaction was concluded the reaction products were used directly to transform TOP10 chemically competent cells.

Plasmid-containing colonies were selected by resistance to the antibiotic kanamycin and positive colonies (those that had the gene inserted into the plasmid) were screened by digestion with restriction enzymes and the resulting fragments were separated by agarose gel electrophoresis. One positive colony was selected for isolation of larger amount of plasmid DNA using the HiSpeed® Plasmid Midi kit (Qiagen). Positive plasmid was introduced by transformation into the expressing cell line Rosetta 2 from Novagen.

Expression and Purification
Protein production (expression) was induced when Rosetta™ 2 cells (Millipore) reached mid-log phase by adding a final concentration of 100 µM of IPTG and incubating over night at room temperature. The following day, protein was purified from inclusion bodies as follows Collect the induced cells by centrifugation and discard the supernatant.
Dissolve cell pellet in 50 mM Tris-HCl buffer (pH 8.0) containing 5 mM EDTA and 1 mM PMSF.
Lyse cells by sonication.
Centrifuge cell lysate at 8000×g for 30 minutes.
Wash pellet with 50 mM Tris-HCl (pH 8.0) containing 5 mM EDTA and 2% deoxycholate.
Centrifuge inclusion bodies and wash again in the same buffer.
Centrifuge inclusion bodies and wash twice with $H_2O$.
Resuspend the final pellet in 100 mM Tris (pH 10.79) to solubilize the enzyme.
Additionally add a final concentration of 1.5M urea to increase yield.

Protein concentration was determined with the Protein Assay Dye Reagent Concentrate (Bio-Rad) using BSA as reference.

Results
GtPheDH was cloned as described herein. The enzyme was subsequently expressed and purified from Rosetta™ 2 cells. FIG. 1 shows purification of GtPheDH from inclusion bodies as described herein. Protein purified from inclusion bodies using this method has a degree of purity of >95% estimated by Coomassie staining (FIG. 1). The purified enzyme was confirmed by Western Blot using polyclonal and monoclonal antibodies. The amino acid sequence of GtPheDH is shown in SEQ ID NO: 1.

Example 2. Characterization of Recombinant GtPheDH

Figure 9A:
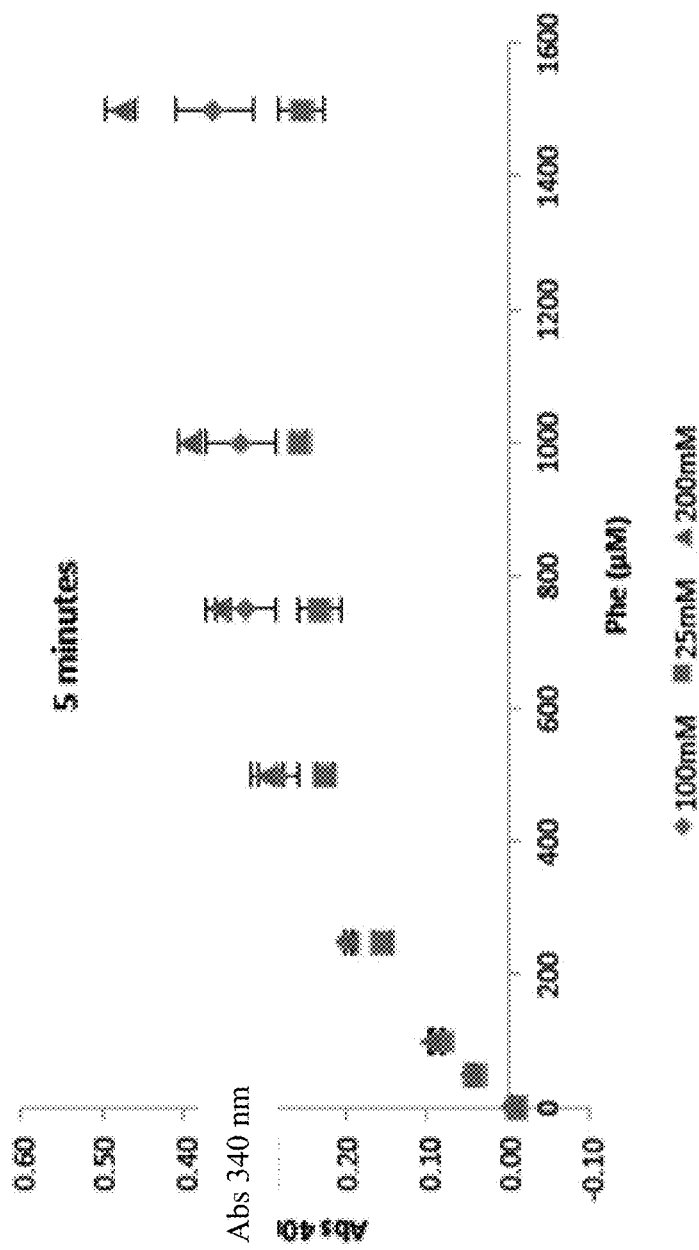
Figure 9C:
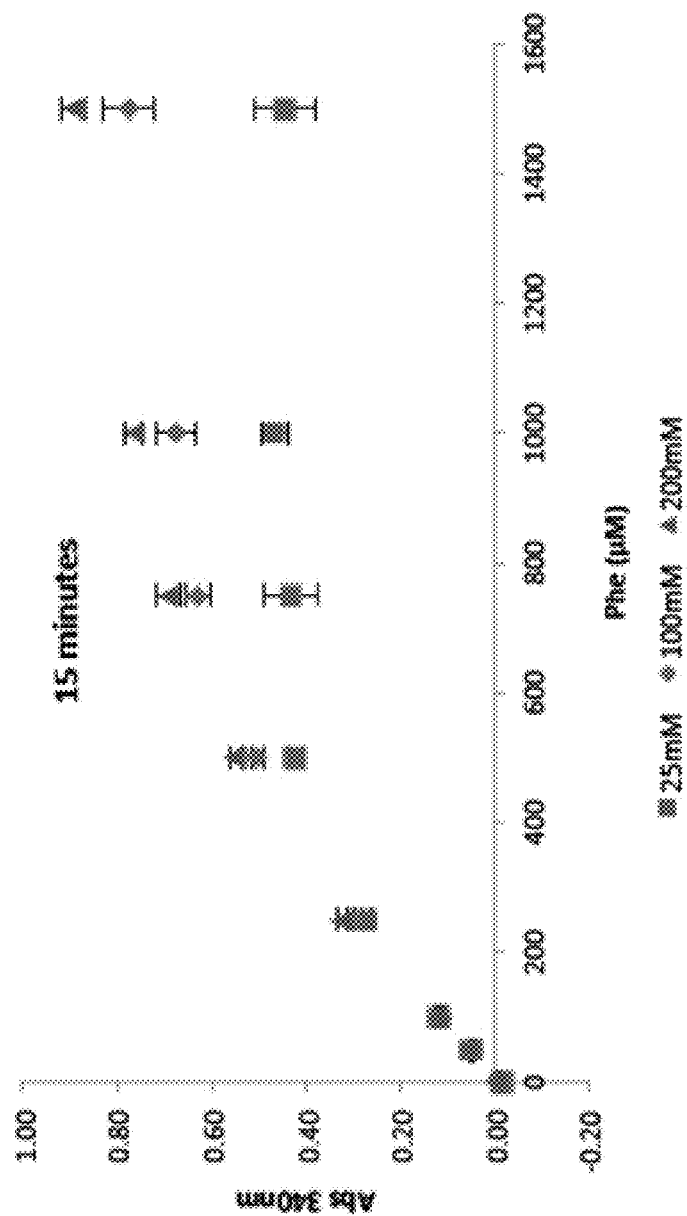

Materials and Methods
Enzymatic Assay
GtPheDH activity was tested for activity in the presence of different concentrations of assay buffer at pH 10.4: 200, 100, and 25 mM Gly/KOH/KCl. The absorbance at 340 nm was measured at different times—5, 10, and 15 minutes after the reaction started—which showed optimal activity at 200 mM Gly/KOOH/KCl (FIG. 9). Thus, assays to measure GtPheDH activity were performed in 200 mM Glycine/KOH/KCl buffer, pH 10.4, containing 0.5 mM phenylalanine and 1 mM NAD. The amount of purified enzyme per 100 µl of assay volume was 1.4 µg. Activity was determined spectrophotometrically by monitoring the production of NADH at 340 nm on a xMark™ spectrophotometer (Bio-Rad).

Additionally, for some experiments, phenylalanine consumption was determined by amino acid analysis using a Hitachi L-8800 amino acid analyzer. Samples were prepared for amino acid analysis as follows:

Add 50 µl of sample to 100 µl of amino acid working solution (62.5 µM aminoethyl-L-cysteine in 0.15M sulfosalicylic acid buffer, pH 2.0).

Incubate on ice for 30 minutes.

Centrifuge samples on a bench-top centrifuge at full speed (~14000 rpm).

Transfer supernatant to vials to be loaded onto the amino acid analyzer.

GtPheDH Stability Assays

Long-Term Storage

GtPheDH was stored for 1 year in 100 mM Tris pH 10.79 at 4° C. at a concentration of 1.4 mg/ml. 1.1 µg of purified GtPheDH were assayed in 200 mM Gly/KCl/KOH buffer pH 10.4 in the presence of 1.25 mM NAD while varying the Phe concentration from 0 to 2.5 mM. The reaction was carried out at room temperature for 5 minutes. Activity was determined by measuring the change in absorbance at 340 nm over time on an xMark™ spectrophotometer (Bio-Rad) using a reference curve of known concentrations of NADH ranging from 0 to 1 mM.

Temperature Effect

For stability assay at higher temperatures, 1.7 µg of purified GtPheDH were assayed in 200 mM Gly/KCl/KOH buffer pH 10.4 in the presence of 1.25 mM NAD while varying the Phe concentration from 0 to 5 mM. The reaction was carried out at room temperature, 45° C. or 55° C. in an xMark™ spectrophotometer (Bio-Rad). Activity was determined by measuring the change in absorbance at 340 nm for 5 minutes.

pH Effect

Figure 3A:
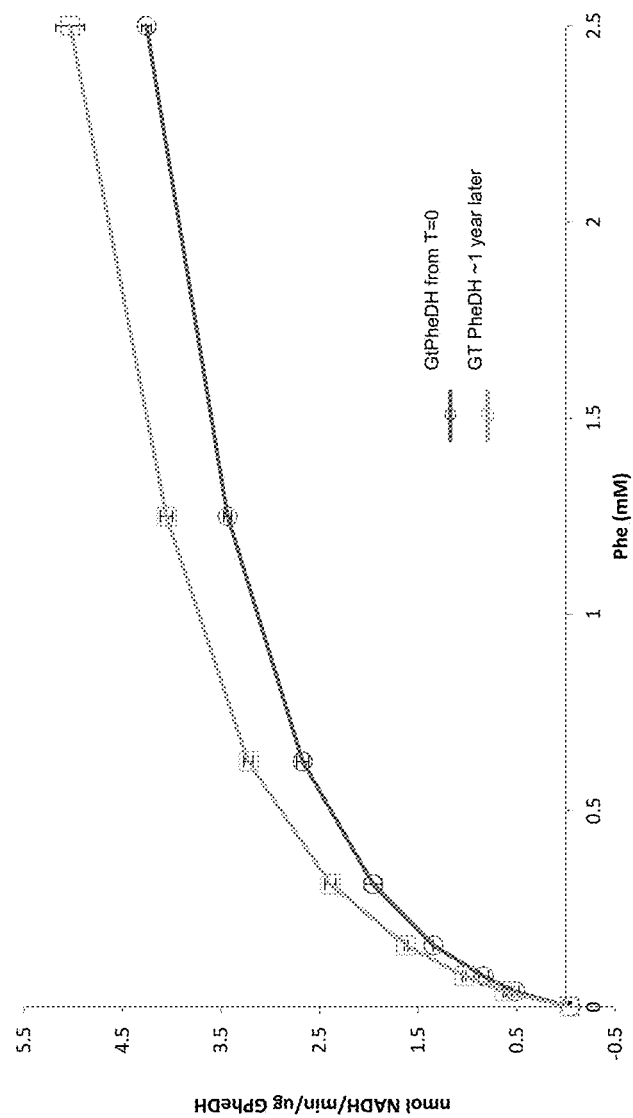
FIGS. 3A-3G are graphs illustrating PheDH enzyme activity after ~1 year of storage (FIG. 3A); at higher temperatures (FIG. 3B); in basic pH; and in simulated gastric fluid (SGF) and simulated intestinal fluid (SIF) (FIGS. 3D-3F).
Figure 3B:
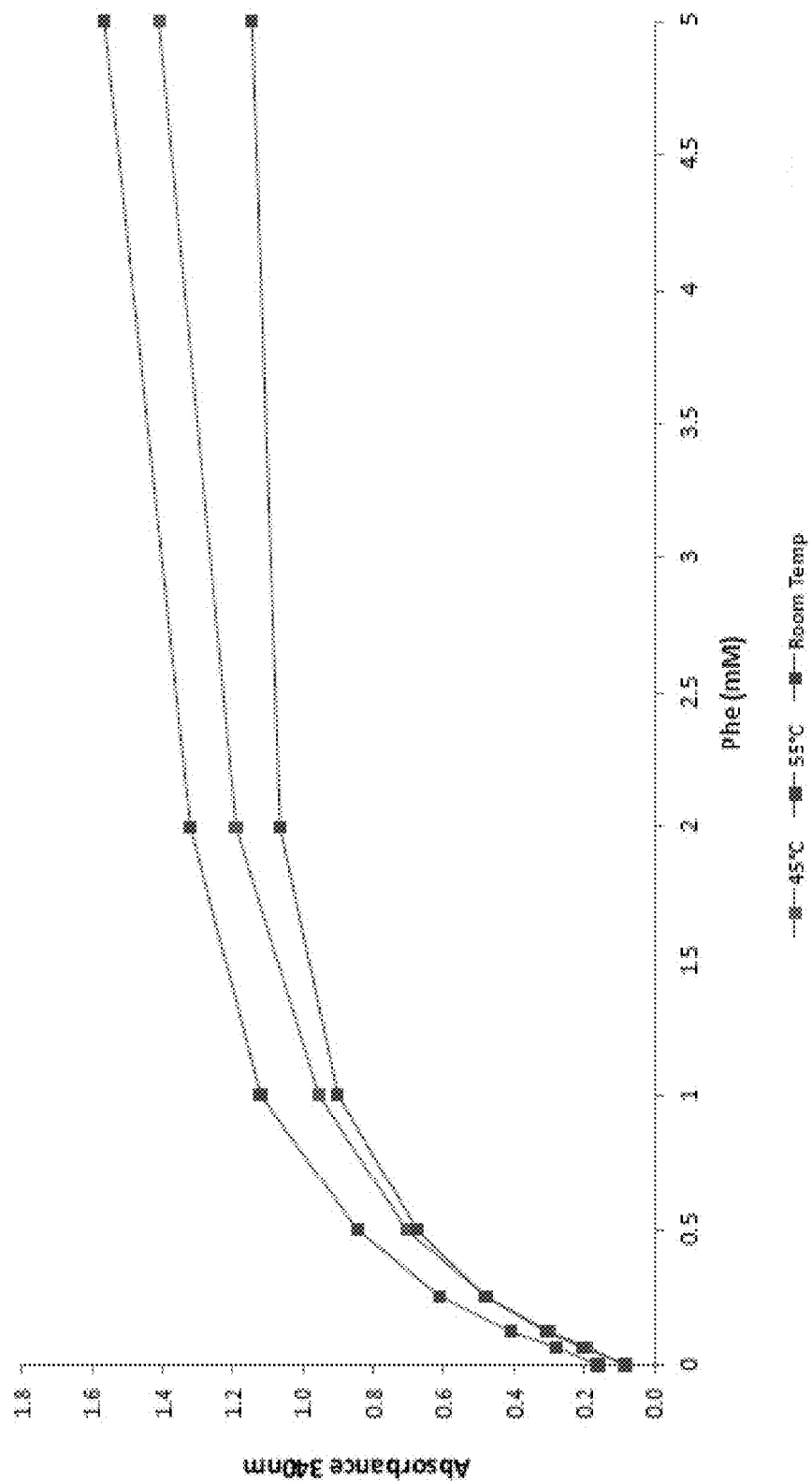
Figure 3C:
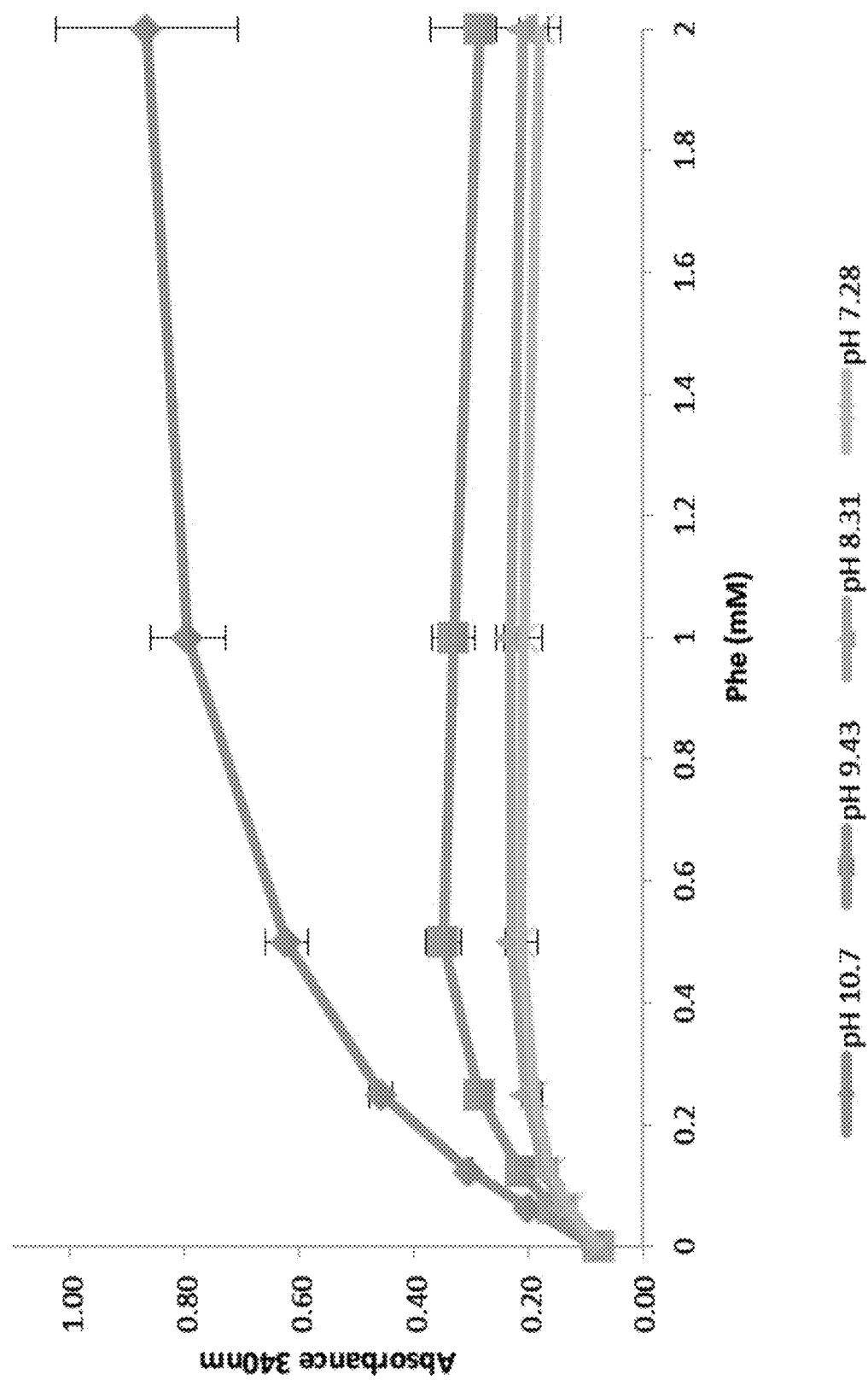
Figure 3D:
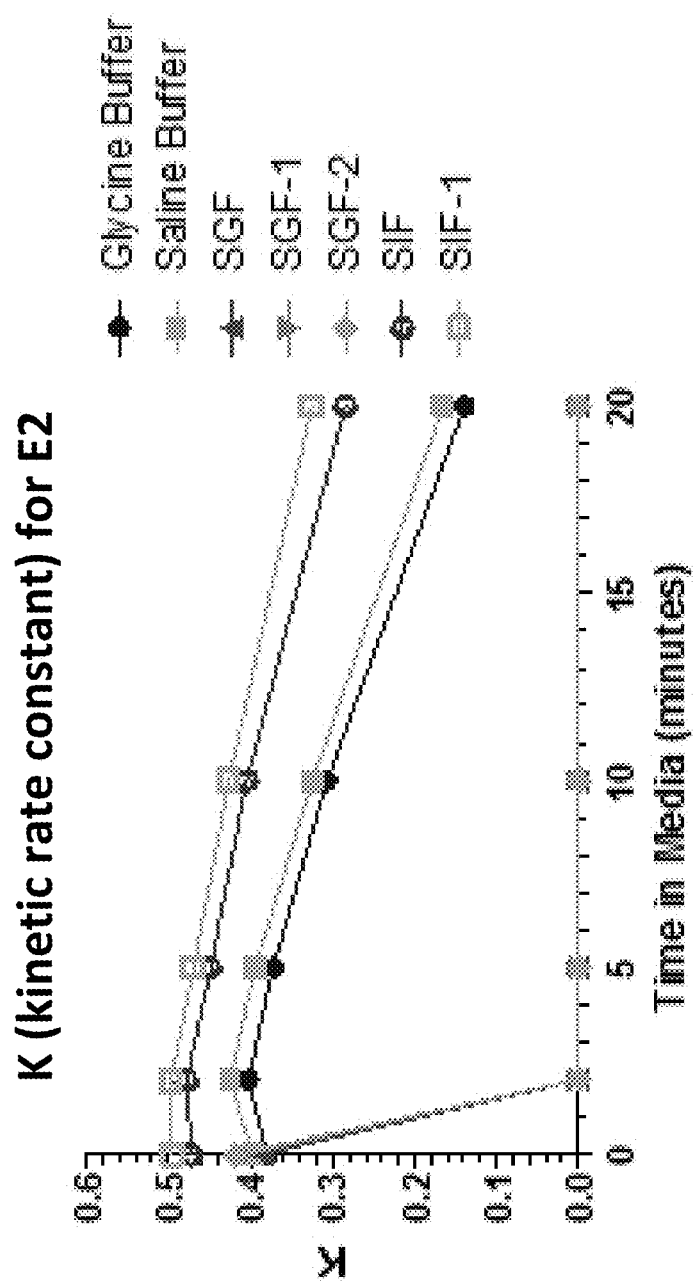

The effect of pH on GtPheDH activity was measured in the presence of different concentrations of Phe and 1.25 mM NAD at different pH in 200 mM Gly/KO/KCl. pH was adjusted with HCl to pH 7.28, 8.31, 9.43, and 10.7 (FIG. 3C). Absorbance at 340 nm was measured after 5 minutes reaction.

Stability in Simulated Gastric Fluid (SGF) and Simulated Intestinal Fluid (SIF)

Two forms of PheDH (E1 and E2) were assessed for stability and activity in SGF (fasted state simulated gastric fluid) and SIF (fasted state simulated intestinal fluid), and to characterize the impact of the biological fluid components (e.g., pepsin, bile salt, pH) on enzyme stability. E1 represents denatured (heat treated) GtPheDH; E2 represents non-denatured GtPheDH in TRIS buffer.

A kinetic UV plate reader method was used for quantifying an enzyme substrate (NAD+) after incubation with the enzyme; substrate quantification served as the indicator of enzyme activity for the study. Stability assessments (inferred from enzyme activity measures) was taken at 37° C. at five time points for each simulated environment (e.g., saline, SGF-1 and SIF), and was referenced to both denatured enzyme and blank (no enzyme) controls. Enzyme kinetics were monitored at 340 nm for 6 minutes after the start of the incubation, with measurements taken every minute, at 37° C. The standard SGF and SIF test media used for evaluations of simulated biological fluids are shown in Table 1.

TABLE 1

SGF and SIF Media

| Component | SGF | SIF |
| --- | --- | --- |
| NaCl | 34.2 mM | 68.62 mM |
| NaOH | — | 34.8 mM |
| Maleic Acid | — | 19.12 mM |
| Sodium Taurocholate | 0.080 mM | 3 mM |
| Lecithin (from Egg Yolk) | 0.020 mM | 0.20 mM |
| Pepsin (from porcine) | 0.1 mg/mL | — |
| HCl | QS to pH = 1.6 | — |
| Deionized water | QS | QS |
| pH | 1.6 | 6.5 |

However, to initially characterize the factors in the gastrointestinal environment, variants of the simulated fluids were evaluated. The seven test media are shown in Table 2. Results were tabulated and graphs fitted according to the equation Y=(Y0−Plateau)*exp(−K*X)+Plateau. The curve fit parameters (robust least-squares fit) used were as follows: Plateau—asymptote level of maximum absorbance (indicates absorbance at maximum substrate conversion); Y0—initial absorbance (proportional to initial substrate level); K—rate constant (measure of kinetic activity). See FIGS. 3E-3F.

TABLE 2

Variants of the simulated fluids

| Component | Glycine Buffer | Saline Buffer | Full SGF | SGF-1 no pepsin | SGF-2 no pepsin, no bile salt | Full SIF | SIF-1 no bile salt |
| --- | --- | --- | --- | --- | --- | --- | --- |
| Glycine | 200 mM | | | | | | |
| NaCl | 200 mM | 300 mM | 300 mM | 34.2 mM | 34.2 mM | 68.62 mM | 68.62 mM |
| KCl | 200 mM | | | | | | |
| NaOH | | | | | | 34.8 mM | 34.8 mM |
| Maleic Acid | | | | | | 19.12 mM | 19.12 mM |
| Sodium Taurocholate | | | 0.080 mM | 0.080 mM | — | 3 mM | — |
| Lecithin (from Egg Yolk) | | | 0.020 mM | 0.020 mM | — | 0.20 mM | — |
| Pepsin (from porcine) | | | 0.1 mg/mL | — | — | — | — |
| HCl | | | QS to pH = 1.6 | QS to pH = 1.6 | QS to pH = 1.6 | — | — |

TABLE 2-continued

Variants of the simulated fluids

| Component | Glycine Buffer | Saline Buffer | Full SGF | SGF-1 no pepsin | SGF-2 no pepsin, no bile salt | Full SIF | SIF-1 no bile salt |
|---|---|---|---|---|---|---|---|
| Deionized water | | | QS | QS | QS | QS | QS |
| pH of Media | 10.3 | 7.4 | 1.6 | 1.6 | 1.6 | 6.5 | 6.5 |
| Media as Portion of Incubation Volume (volume percentage) | 33% | 33% | 33% | 33% | 33% | 33% | 33% |
| Test Enzyme Conc. (during incubation with substrate) | 67 ug/mL | 67 ug/mL | 67 ug/mL | 67 ug/mL | 67 ug/mL | 67 ug/mL | 67 ug/mL |
| Estimated pH During Incubation | ~10 | ~9 | ~8 | ~8 | ~8 | ~9 | ~9 |

Assay Procedure:

1) Reagents (media, 3 mM NAD in buffer, 3 mM Phe) were prepared fresh prior to testing; buffer condition 200 mM Gly/KOH/KCl was used.

2) For each timepoint and each media specified, the substrate and NAD were added to each well in the plate, to which a) 100 µL of 3 mM NAD in buffer and b) 100 µL of 3 mM Phe in buffer were added.

3) For each media and each test enzyme, in separate glass vials, 775 µL of media was added to the vial.

4) [At T=0] For each media and each test enzyme, 225 µL of enzyme (E1 and E2 at 900 µg/mL, or blank which is buffer only) was added to the vial (final well volume 300 µL, final enzyme concentration 67 µg/mL). Vials were vortexed 3 seconds. This starts the stability timing [T0].

5) At each timepoint specified for each vial (test enzyme in media), 100 µL was removed from the vial and placed into an Eppendorf tube and immediately frozen in liquid nitrogen for later testing; 100 µL was removed from the vial and placed into the appropriate well (the correct well marked for the given timepoint) on the plate (containing NAD/Substrate). The samples were read under UV.

6) The plate was returned to the UV reader for 6 minutes (360 seconds in plate reader at 37 C). The plate was gently shaken for 15 seconds prior to reading. Read absorbance at 340 nm every 60 seconds.

7) Steps 5 and 6 were repeated for each timepoint of interest.

Figure 4:
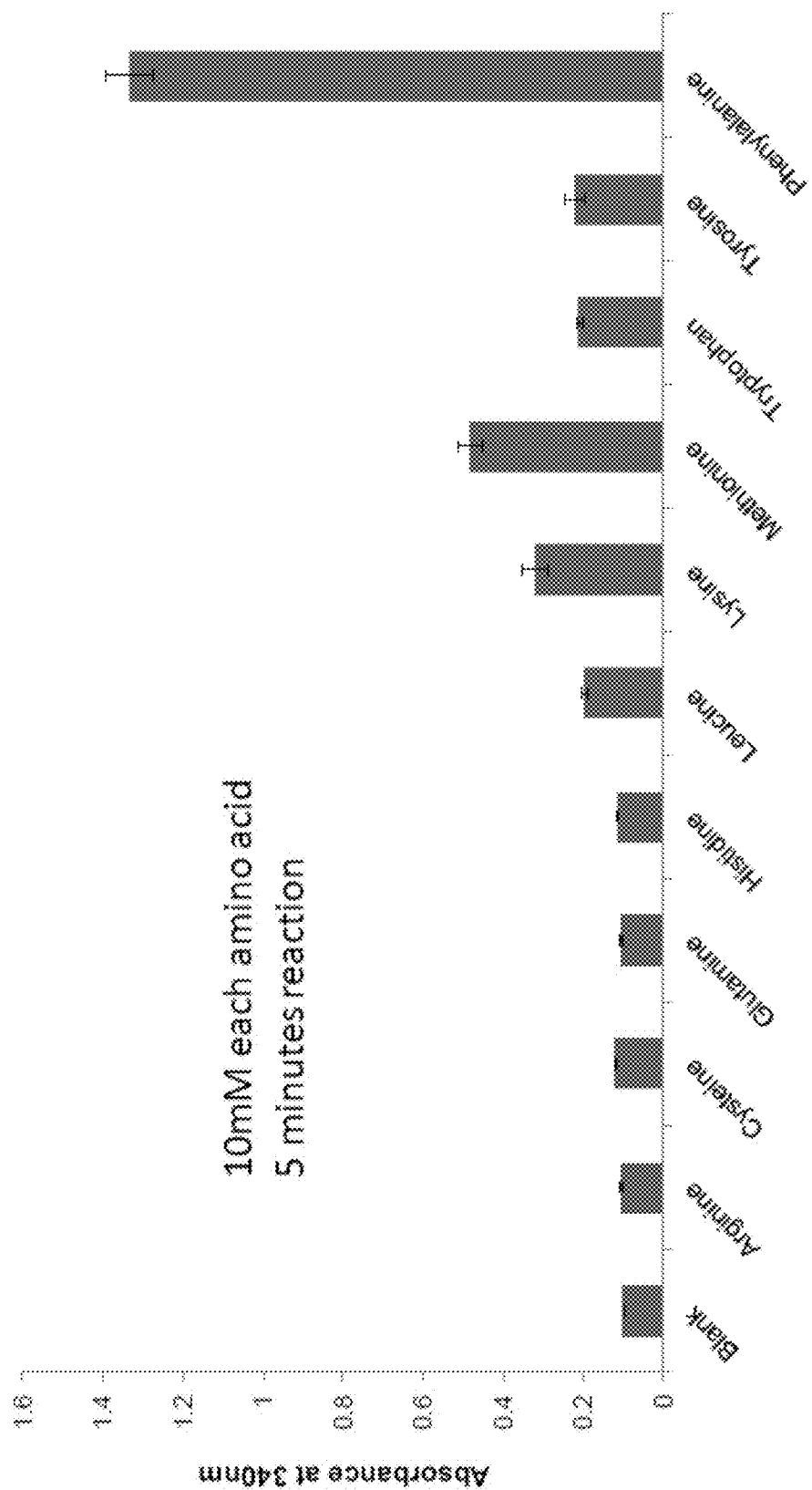
FIG. 4 is a graph illustrating selectivity of the GtPheDH enzyme for Phe as compared to other amino acids (demonstrating 2.5-12.5 times greater selectivity for Phe).

GtPheDH Specificity Assay 1.7 µg of purified GtPheDH were assayed in 200 mM Gly/KCl/KOH buffer pH 10.4 in the presence of 1.25 mM NAD and 10 mM of each amino acid shown in FIG. 4. The reaction was carried out at room temperature and activity was determined by measuring the change in absorbance at 340 nm after 5 minutes using an xMark™ spectrophotometer (Bio-Rad).

Results

Figure 2A:
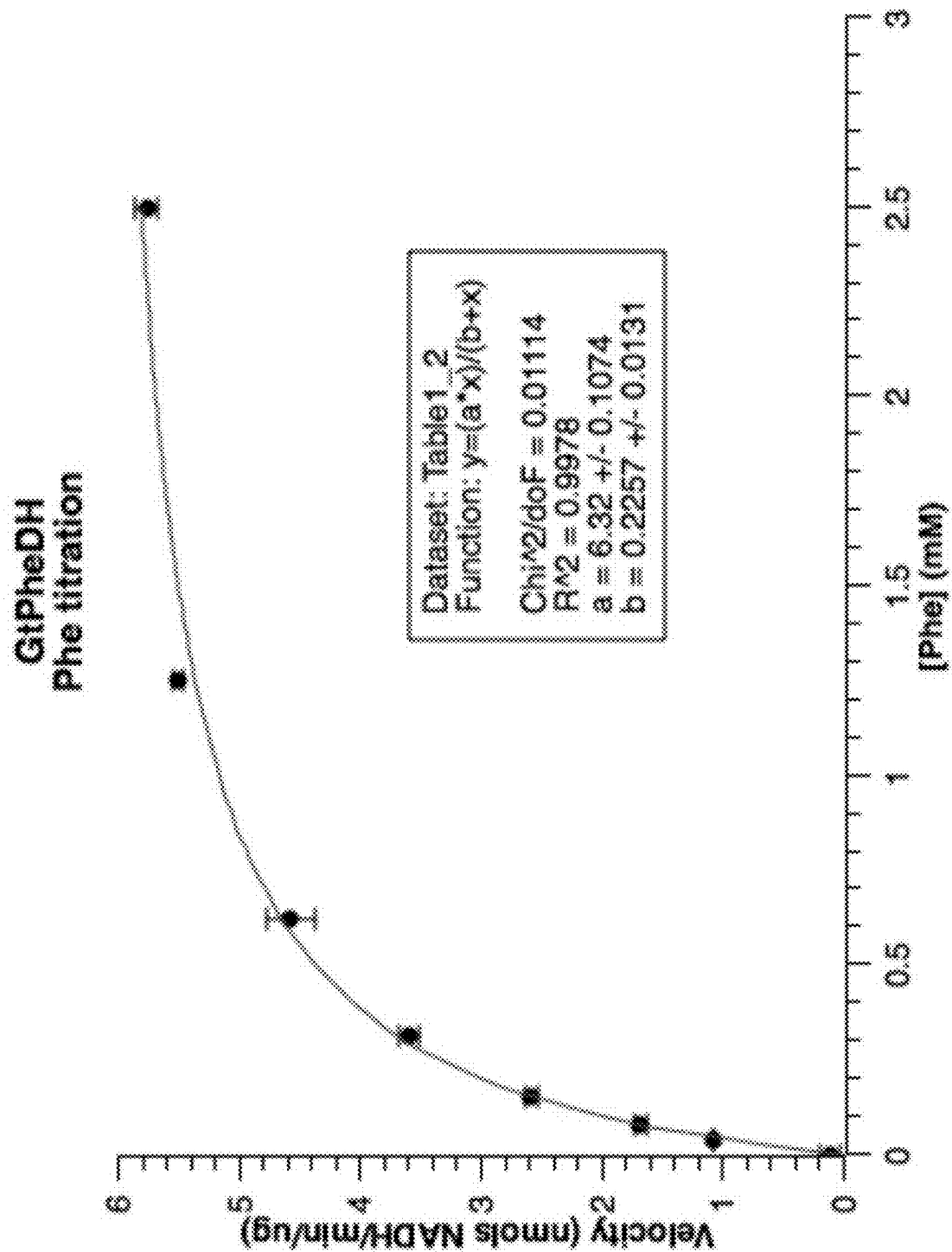
FIGS. 2A and 2B show the results of GtPheDH kinetic assays.
Figure 2B:
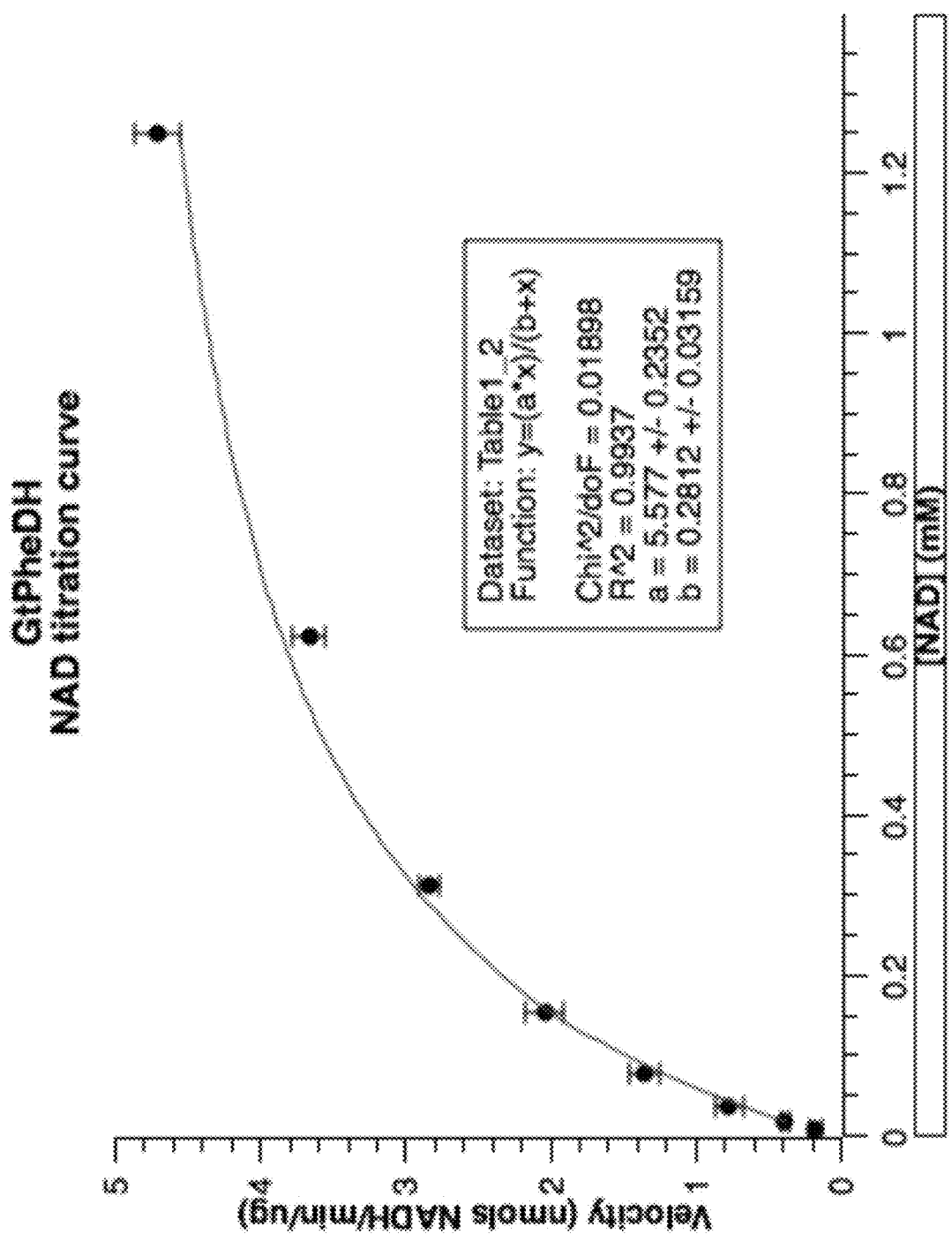

GtPheDH purified in Example 1 demonstrated efficient conversion of phenylalanine to phenylpyruvate in the presence of NAD$^+$, based on measurement of NADH formation as a readout (see FIGS. 2A and 2B). GtPheDH was found to be 2.5-12 times more selective for phenylalanine over other tested amino acids (FIG. 4). Additionally, GtPheDH stored in 100 mM Tris pH 10.79 at 4° C. at a concentration of 1.4 mg/mL retained enzymatic activity after about 1 year in storage (FIG. 3A). Further, the enzyme is thermostable, up to at least about 55° C. (FIG. 3B). As shown in FIG. 3C, GtPheDH possessed the highest activity at pH 10.7; a significant drop in activity was measured at pH 9.43. GtPheDH demonstrated activity in saline as well as in water.

Figure 3E:
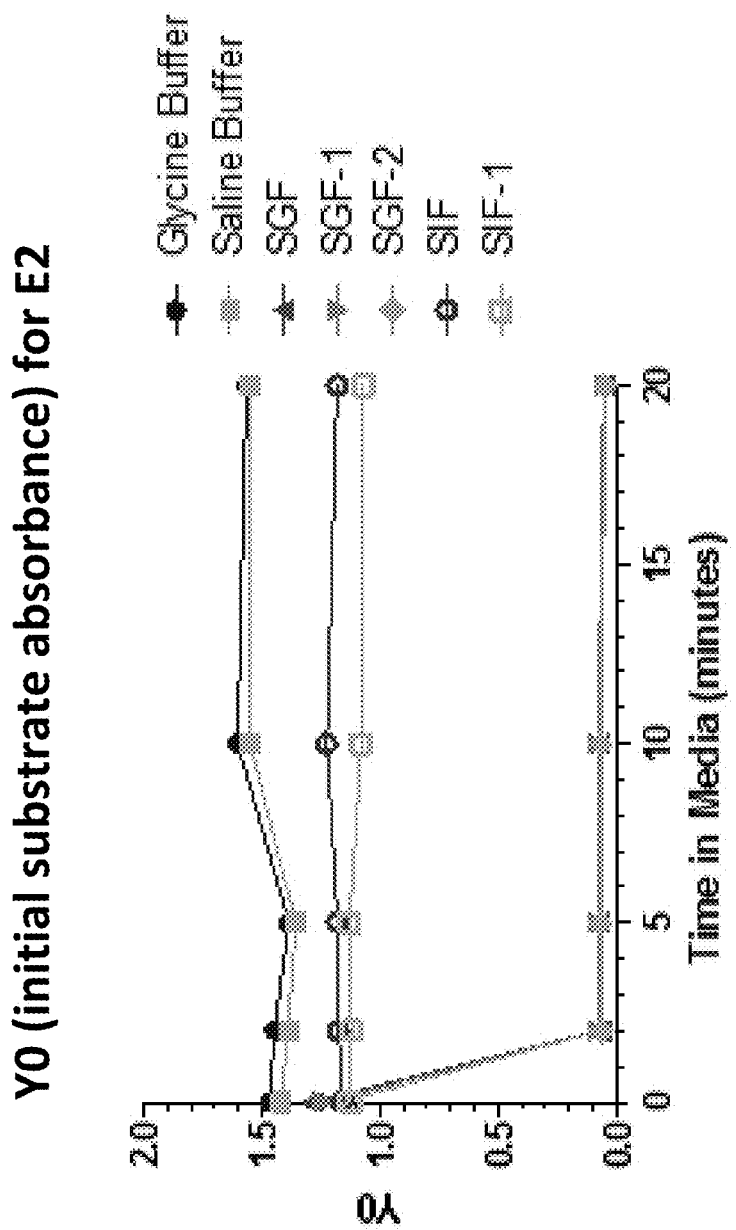
Figure 3F:
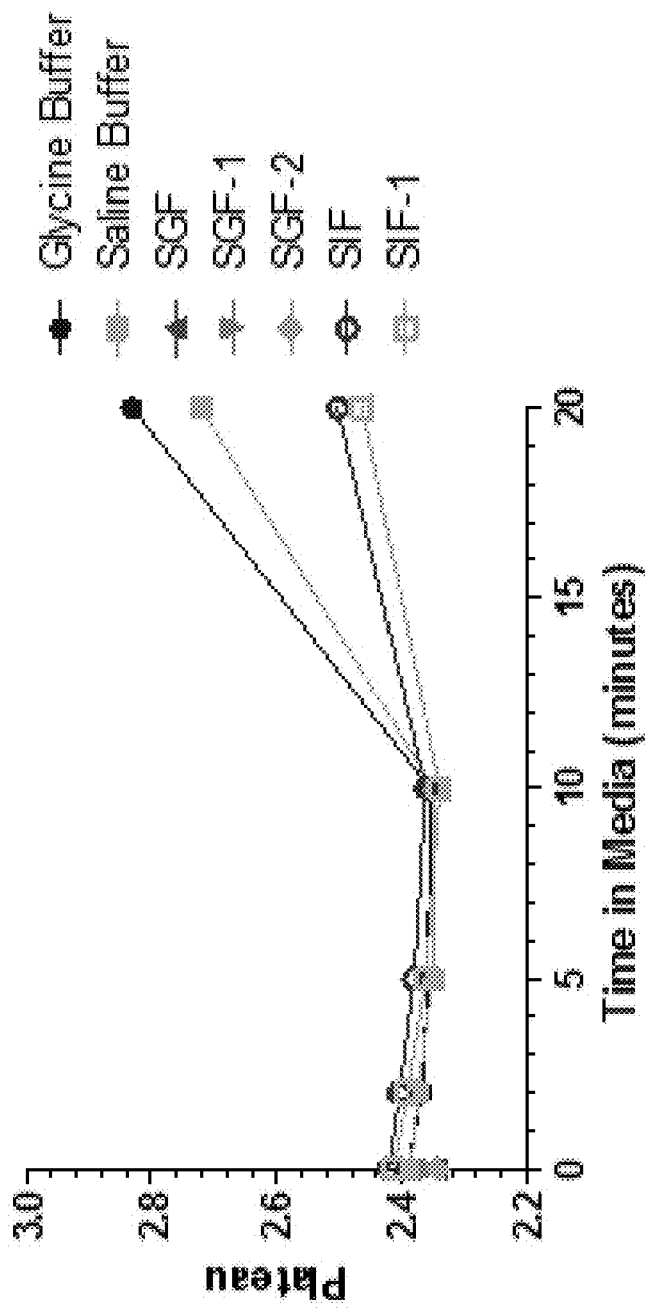
Figure 3G:
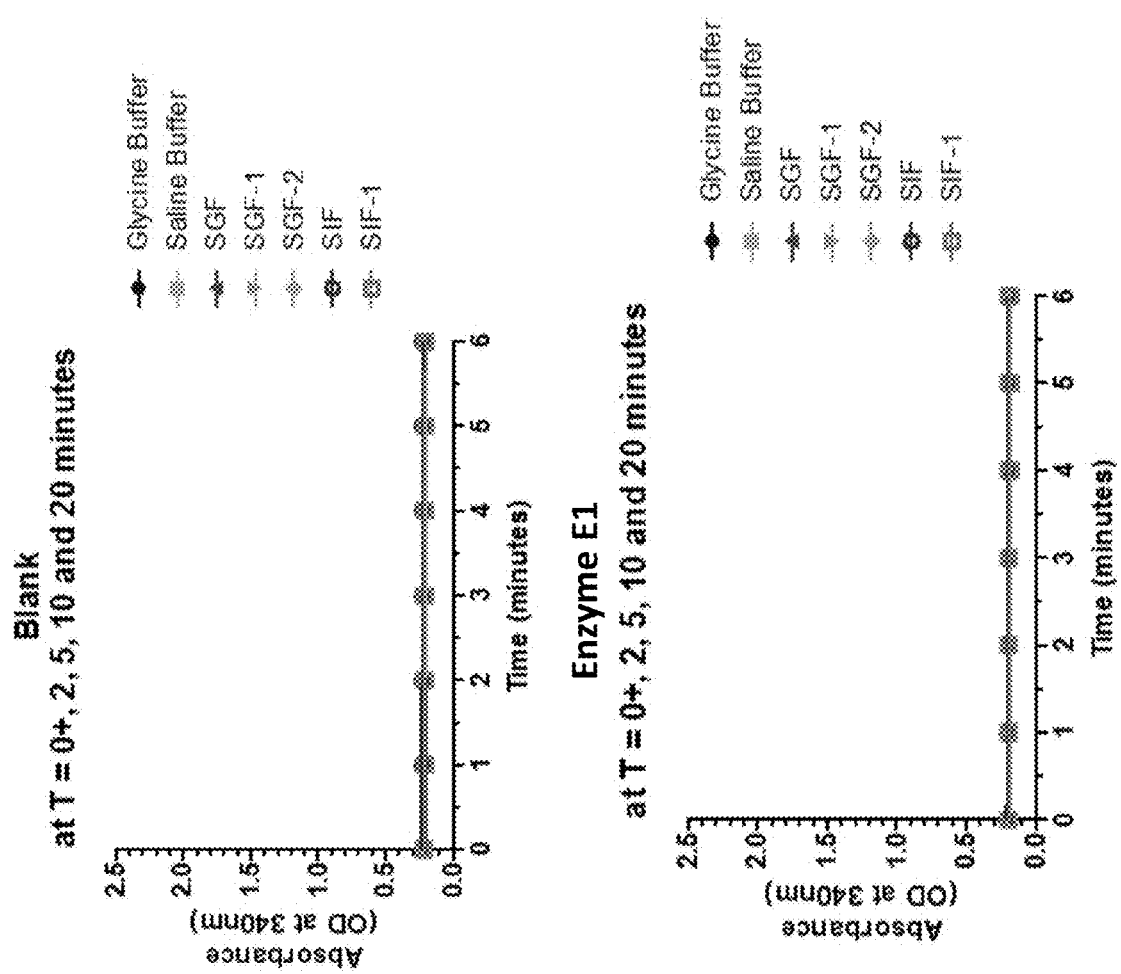

As shown in FIG. 3E, enzyme E2 did not show activity in all SGF media tested (SGF, SGF-1, and SGF-2) after T0. In contrast, E2 showed greater activity in SIF and SIF-1 (with 70-75% initial activity after 20 minutes in the media). No difference was observed between SIF and SIF-1 (without bile salt). E2 exhibited high enzyme activity in glycine and saline (45-50% initial activity after 20 minutes in the media). Blank and enzyme E1 exhibited no activity across all tested media at the indicated hold times (FIG. 3G).

Example 3. Reduction of Phe Concentration in the Intestine in a Wild-Type Mouse Model Mice Housing Wild-type C57BL/6 mice were obtained from Children's National Medical Center (CNMC), and housed in the animal facility at CNMC.

Luminal Content Extraction

Figure 5A:
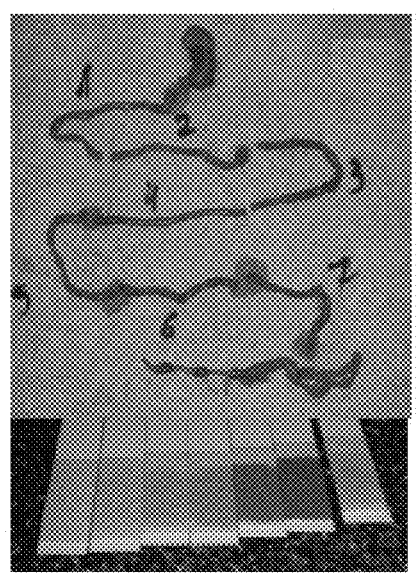
FIGS. 5A and 5B depict intestine sectioning and amino acid level monitoring in C57BL/6 wild-type mice.
Figure 5B:
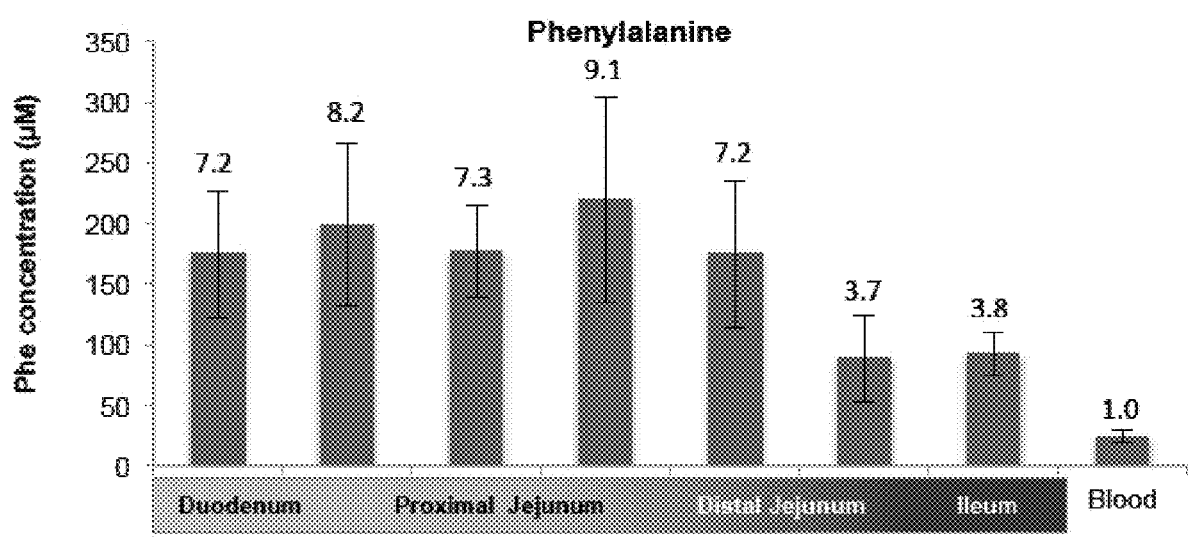

Wild-type C57BL/6 mice were sacrificed by CO2 inhalation and death was ensured by cervical dislocation. Intestinal tract was harvested from the stomach to the rectum and placed on a paper towel as shown in FIG. 5A. The intestinal tract was sectioned in 7 portions as shown in FIG. 5A and the contents of each section were flushed with 500 µl of H$_2$O. Each section-flushed content was incubated rotating at room temperature for 30 minutes and the soluble materials were separated from the solids by centrifugation. The pH of each section was measured using the soluble fraction of each sample by pH paper as shown at the bottom of FIG. 5B (yellow: acid, blue: basic).

Figure 6:
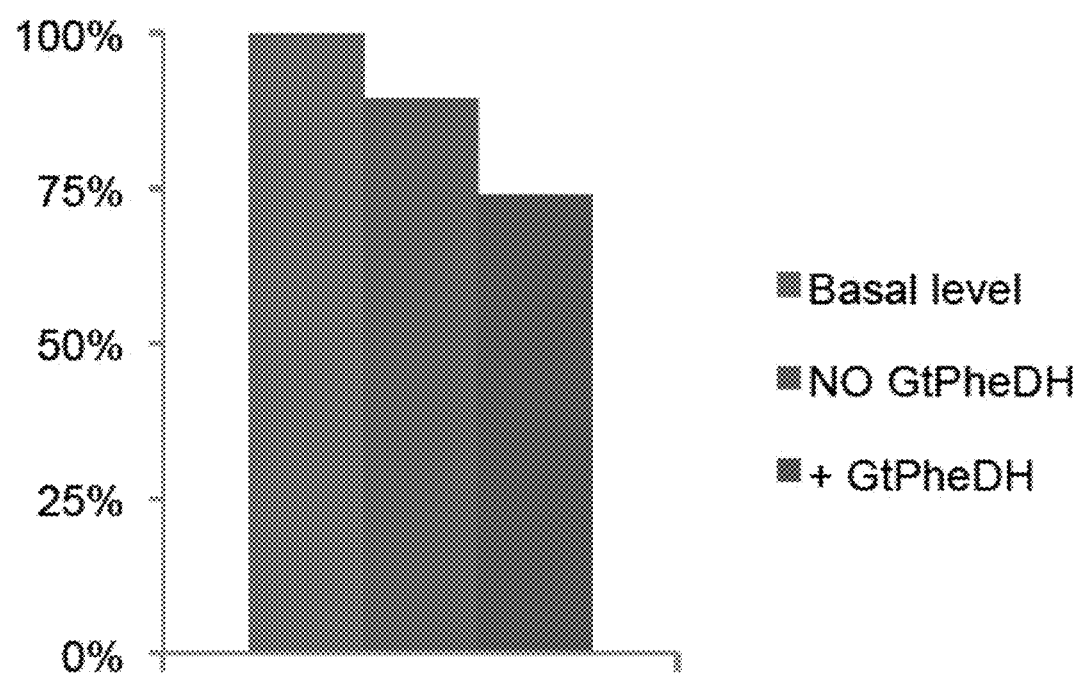
FIG. 6 is a graph depicting consumption of free Phe in the luminal content of mice (in section "5" of the intestine, as shown in FIG. 5A; section 5 has a basic pH). GtPheDH reduced free Phe levels by more than 25% under the conditions tested.

Phenylalanine content in each section was measured by amino acid analyzer (Hitachi L-8800) in the soluble fraction described in FIG. 5A. Bars represent the average concentration in µM of an n=6 or higher±the standard deviation for each section. The number above each bar shows the difference with the blood Phe concentration (FIG. 6).

Assay for Luminal Phe Reduction by GtPheDH

Phenylalanine content in each section was measured by amino acid analyzer (Hitachi L-8800 and/or 8900) in the soluble fraction described in FIG. 5A. Bars represent the average concentration in μM of an n=6 or higher±the standard deviation for each section. The number above each bar shows the difference with the blood Phe concentration (FIG. 5B).

The soluble fraction of section 5 shown in FIG. 5A was used to test the ability of GtPheDH to reduce the concentration of Phe in the intestinal tract. Phe levels were measured using an amino acid analyzer (Hitachi L-8800 and/or 8900) at time 0 and at time 30 minutes both in the absence or presence of 1.7 μg of purified GtPheDH per 100 μl of soluble fraction.

Results

The amount of free amino acids in the intestine of wild type C57BL/6 mice (6 weeks old) fed standard mouse chow (18% protein content) was determined. FIG. 5B shows the concentrations of Phe along the length of the intestine. The trend shown in FIG. 5B is in agreement with progressive amino acid absorption in the digestive tract. As shown in FIG. 5B, the concentration of free Phe in some of the intestinal sections shown in FIG. 5A can be up to more than 10 times higher than that of blood.

Further, the ability of GtPheDH to reduce the free Phe levels present in the luminal content of mice was examined. As shown in FIG. 6, GtPheDH is capable of reducing free Phe levels by more than 25% under the conditions tested (section 5 as shown in FIG. 5A; section 5 has a basic pH).

Example 4. Reduction of Phe Concentration in the Intestine and Blood in a Mouse Model of PKU Materials and Methods
Mouse Model Several murine models of PKU have been previously described and characterized. The studies described herein use the BTBR-Pah$^{enu2}$/J strain (Pascucci, T. et al., *PloS One* 8, 384697, 2013), which has been successfully used to study hyperphenylalaninemia (HPA). The results obtained with this model are representative of the relationship between the amount of Phe in the intestine and that of blood in PKU patients, and allows for evaluation of the efficacy of GtPheDH to control intestinal Phe levels, and therefore, Phe levels of blood.

Phe levels in the intestine and blood are evaluated as a function of diet. At 4 weeks of age, BTBR-Pah$^{enu2}$/J wild type mice diet is changed to different protein-adjusted diets ("protein free", 6%, 20% and 40%) for two weeks. Meanwhile, homozygous BTBR-Pah$^{enu2}$/J (Gropper, S., et al., *Molecular Genetics and Metabolism*, 82:76-82, 2004) mice are maintained on a Phe-free diet and receive Phe in their drinking water (0.7 gr/L as described previously—see Gropper, S., et al., *Molecular Genetics and Metabolism*, 82:76-82, 2004). During this time, blood samples are collected once a week from the submandibular vein to monitor serum Phe levels. At the end of the experimental period, Phe and other amino acids present in the blood and intestinal sections (see, for example, FIG. 5A) are quantified as described in the methods described herein using an amino acid analyzer (Hitachi L-8800). Likewise, Phe is measured in the brain and other tissues to determine how the concentration in the serum affects Phe concentrations in different tissues.

Mice Housing

BTBR-Pah$^{enu2}$/J mice are obtained from Jackson Laboratories, Bar Harbor Me. (stock 002232) and housed in the animal facility at Oregon Health Sciences University. Husbandry conditions for the mice have been previously described (Ding et al. Gene Therapy 2006 13:587-593). To avoid the effects of maternal PKU on the pups the colony is maintained by breeding heterozygous BTBR-Pah$^{enu2}$/J females with homozygous males kept on a low-Phe diet (Phe-free chow from Harlan Teklad TD97152 with supplemental LPhe in the drinking water at 0.7 g/L) to keep the serum Phe concentrations at a safe level (Gropper, S., et al., *Molecular Genetics and Metabolism*, 82:76-82, 2004). Mice will be genotyped according to known methods, e.g., single-nucleotide polymorphism genotyping.

Luminal Content Extraction

Mouse intestines are harvested from the stomach to the caecum and divided in 3-6 regular sections (as shown in, e.g., FIG. 5A). The contents of each section of the intestine are flushed two times with 250 μl (each) of water and collected in a 1.7 ml centrifuge tube. Subsequently, each sample is incubated at room temperature for 30 minutes under rotation. The solid materials are separated by centrifugation at ~14000×g for 5 minutes while the supernatant, containing the soluble material is transferred to a fresh container for analysis of amino acid levels. Flushed intestines are processed further to evaluate, e.g., GtPheDH-mediated Phe reduction.

Assay for Luminal Phe Reduction by GtPheDH

The capacity of GtPheDH to reduce the amount of free Phe is evaluated, in vitro, using conditions specific to each portion of the intestine (pH and soluble nutrients). GtPheDH dosage is determined empirically based on the results obtained with each amount of enzyme tested. Initially, 5 μg of purified GtPheDH is added to each sample in the presence or absence of NAD$^+$ and incubated at 37° C. for at least 2 hours. To determine the duration of the dehydrogenase activity and the amount of free Phe consumed over time, aliquots are taken every 15-20 minutes and Phe concentrations are measured as described herein using an amino acid analyzer. GtPheDH levels, and therefore stability, are assessed by western blot using a custom antibody, which has a high specificity for this enzyme, that was developed in rabbit using Bio Synthesis Inc. services.

Blood Collection

Blood is spotted onto filter paper (Whatman® 903 Protein Saver Cards) once a week from the submandibular vein for monitoring Phe levels. At the end of the experimental period, after euthanasia and before exsanguination, blood is collected from the heart and centrifuged at 4 degrees to separate the serum for amino acid quantification. The level of Phe in dried blood spots is analyzed as described in Allard et al. (*Clinical Biochem.* 37:857-862, 2004) using single ion monitoring and stable isotope reference mass spectrometry.

Amino Acid Quantification

Each sample to be analyzed is mixed (1:2 ratio) with the amino acid working solution (62.5 μM aminoethyl-L-cysteine in 0.15 M sulfosalicylic acid buffer, pH 2.0) and incubated on ice for 30 minutes. Precipitated proteins are separated by centrifugation at 16000×g for 10 minutes and the supernatant containing the free amino acids is loaded into an amino acid analyzer (e.g., Hitachi L-8800 and/or 8900) for quantification.

Tissue Extraction

At the end of the experimental period, tissues are collected after euthanasia and snap-frozen in liquid nitrogen for further analyses.

Immunohistochemical Analyses of Intestinal Sections

A longitudinal portion of each of the intestinal sections obtained as described herein is fixed and preserved in paraffin for immunohistochemical analyses. At the same time another portion is used for expression analyses by Western blot and Real Time qPCR. Commercially available antibodies is used to determine the expression levels of the various amino acid transporter systems ($B^0$, $B^{0,+}$, $b^{0,+}$, IMINO, β, $X_{AG}^-$, ASC, N and PAT) by Western blot and immunohistochemistry. Primers are designed for each of the transporter systems for mRNA expression studies by Real Time qPCR. Expression levels of the different transporter systems both at the protein and mRNA levels are quantified along the length of the intestine in these mice providing a snapshot of the biologic response of the amino acid uptake system to dietary changes.

Protein Extraction, Quantification, Western Blot, and Immunohistochemistry

Protein extraction, protein quantification, Western blot, and immunohistochemistry are performed following standard protocols.

Antibody Production for Immunoassays

The antibodies described herein were generated by inoculating rabbit or mice with a purified GtPheDH (SEQ ID NO: 1), or fragments thereof (e.g., underlined sequences of SEQ ID NO: 1). Candidates were screened using ELISA-based binding to the immunogen. Antibodies having the desired characteristics (e.g., binding to GtPheDH immunogen) were isolated using routine methods.

RNA Extraction and Real Time qPCR

Total RNA is extracted from each sample using Trizol® following the manufacturer recommendations. cDNA is synthesized from 1 μg of total RNA using the iScript™ cDNA Synthesis Kit (Bio-Rad). Real Time qPCR is performed using the iTaq™ Universal SYBR® Green Supermix (Bio-Rad) from 50 ng of cDNA on a 7900HT Fast Real-Time PCR System (ABI) and analyzed using the SDS 2.4 software (ABI).

Statistical Analyses

Blood and intestinal amino acids concentrations within each group are compared to control values using Student's t test assuming equal variances and by repeated measures analysis of variance. For comparison of means between treatment groups, analysis of variance is utilized assuming parametric data. If the data is non-parametric, the Kruskal-Wallis test is utilized. The data are summarized as means+/−standard deviation.

Example 5. Modified GtPheDH with Improved Function and/or Stability

Materials and Methods
Protein Identification

The bands detected by Western blot are sliced and each slice is digested by trypsin and the resulting peptides analyzed using our automated LC-MS and MS/MS system (nano-LC Paking connected to Thermo-Electron LTQ mass spectrometer).

Protein Modifications

Protein modifications are performed as described previously (citations 32-34).

Expected Results

The capacity of GtPheDH to reduce intestinal concentrations of Phe, in vitro, is determined as described herein. However, this capacity could be reduced due to several factors, e.g., suboptimal conditions existing in the intestinal lumen, or degradation of GtPheDH in the presence of certain digestive enzymes of the gastrointestinal tract. GtPheDH can be modified to circumvent such scenarios. For example, at 30 minutes intervals, an aliquot of the intestinal sample being exposed to GtPheDH (e.g., during the luminal Phe reduction assay described herein) is checked for the presence of GtPheDH by Western blot using a custom antibody. If smaller size bands are found, such fragments are sequenced to identify the fragments. The results obtained identify the potential digestion products and thus the regions of the protein that may need to be protected. Previously, other dehydrogenases have been modified to increase their stability and resistance to different environments (Luschak, *Biochem. and Mol. Biol. Int'l* 44:425-432, 1998; Yoshimoto et al., *Enzyme and Microbial Tech.* 49:209-214, 2011; Zhou et al., *Int'l J. of Biol. Macromolecules* 47:21-26, 2010). Such modifications include, e.g., immobilization on hybrid alginate-chitosan beads or polyethylene glycol (PEG) and encapsulation in liposomes. GtPheDH can be modified as described for other dehydrogenases (citations 32-34) as needed, and its stability and ability to reduce Phe concentrations in the intestinal tract portions collected can be re-evaluated according to the methods described herein.

Example 6. Characterization of GtPheDH Variants Having Improved Activity

Materials and Methods

Activity screening in Simulated Intestinal Fluid (SIF) (DNA 2.0, Newark, Calif.)

Six different GtPheDH variants, designated Variant 1 through Variant 6 (V1-V6), were expressed in *E. coli* and purified by immobilized metal affinity chromatography (IMAC) on TALON (GE Life Sciences) resin. Purified proteins were normalized in concentration for subsequent assays at a concentration of 250 μg/ml. Activity was assessed at pH 5.5-6.5 in simulated intestinal fluid (SIF) containing 1 mM NAD+ at 25° C. Reactions were initiated by adding phenylalanine (Phe) to a final reaction concentration of 2 mM. Analysis was performed on a spectrophotometer at 340 nm with results represented as μM/min reaction rates.

Amino Acid Selectivity (DNA 2.0, Newark, Calif.)

The assay was done to evaluate the specificity of the variant activity to Phe compared to other amino acids including leucine and tyrosine. Assays were performed as described above at pH 6.6 with the replacement of each of the other amino acids at 2.0 mM as the reaction substrate. Variants were tested at a concentration of 250 μg/mL with the exception of V4, V5, and V6, which were both tested at 1000 μg/mL.

pH Profiling (PharmOptima, LLC, Portage, Mich.)

This assay was executed to profile the range of activity of the variants across a range of pH environments. Variants were tested at 1 μg in 0.1M Tris at pH 8.0. The assay buffer was 0.1M MES for pH 5.5-6.5, and 0.1M HEPES at pH 7-8. The assay was prepared as described above with OD/sec representing initial velocity $V_0$ in kinetic scanning mode.

Reversible pH Deactivation (PharmOptima, LLC, Portage, Mich.)

This assay was conducted to assess the ability of the variants to recover activity after exposure to lower pH that simulate gastric and upper intestinal environments. PheDH variants at 1 μg were incubated in buffer at a pH 3, 3.5, 4, 4.5, 5, 5.5, 6, 6.5, 7, and 8 for one hour at 37° C. For pH ranges from 3-3.5, a 0.25M glycine buffer was used, and for pH ranges 4-8 a 0.1 M citrate buffer was used. Following the one hour incubation the PheDH variants were assessed for activity as described above.

Protease Sensitivity (PharmOptima, LLC, Portage, Mich.)

This assay was performed to evaluate the sensitivity of the variants to gastric and intestinal protease digestion. Variants at 1 µg were diluted into the given assay buffer for one hour at 37° C. Proteases were used at a 10:1 weight ratio, e.g. 2.0 µg PheDH, 200 ng protease. For pepsin a 0.25M glycine buffer was used at pH 3.5. For trypsin and chymotrypsin a 0.1M MES buffer at pH 6.5 was used. Samples were tested in the spectrophotometric assay as described above as well with data represented as OD as in 10% Bis-Tris SDS gels to demonstrate the presence of intact protein (data not shown).

Results

Variants V1-V6 were tested in simulated intestinal fluid (SIF) to screen their ability to consume Phe. Generally the variants displayed activity with increasing pH, with a 14-22 fold increase in activity from pH 5.5 to pH 6.5 in V2, V3, and V4 (see Table 3). These data indicate the variants are active in a physiologically relevant matrix.

TABLE 3

Variant Phe Activity in Simulated Intestinal Fluid (SIF)

| pH | V1 | V2 | V3 | V4 | V5 | V6 |
|---|---|---|---|---|---|---|
| 5.5 |  | 0.012 | 0.020 | 0.023 |  |  |
| 5.6 |  |  |  | 0.034 | 0.067 | 0.072 |
| 5.7 | 0.012 | 0.010 | 0.014 | 0.056 | 0.093 | 0.110 |
| 5.9 |  | 0.014 | 0.016 | 0.054 |  |  |
| 6.05 |  |  |  | 0.17 | 0.250 | 0.189 |
| 6.1 |  | 0.062 | 0.059 | 0.14 |  |  |
| 6.5 | 0.264 | 0.228 | 0.294 | 0.52 |  |  |

Data are presented in initial velocity $V_0$ as µM/min.

The variants were also tested for their substrate selectivity to Phe in pH 6.6 SIF compared to other amino acids. Activity for Phe was 4.5-28 fold greater compared to Leucine and 7-138 fold greater than for Tyrosine (see Table 4).

TABLE 4

Variant Amino Acid Selectivity in Simulated Intestinal Fluid (SIF)

| Amino Acid | V1 | V2 | V3 | V4* | V5* | V6* |
|---|---|---|---|---|---|---|
| Phenylalanine | 0.264 | 0.55 | 0.52 | 1.08 | 1.11 | 1.00 |
| Leucine | 0.045 | 0.020 | 0.024 | 0.15 | 0.21 | 0.22 |
| Tyrosine | 0.036 | 0.004 | 0.007 | 0.11 | 0.15 | 0.14 |

Variants V1, V2, V3 were tested at concentrations of 250 µg/mL.
*Variants V4, V5, and V6 were tested at a concentration of 1000 µg/mL. Data is presented in initial velocity $V_0$ as µM/min.

Variants tested across a range of pHs displayed differential activities. Some variants like V1 and V1 had little activity below pH6, while V4 had similar values across pHs indicating stability of activity. Overall there was an increase in Phe activity of 56-620 fold between pH 5.5 to 8 among the variants (see Table 5).

TABLE 5

Variant Activity Profile Across pHs

| pH | V1 | V2 | V3 | V4 | V5 | V6 |
|---|---|---|---|---|---|---|
| 5.5 | 0.000001 |  |  | 0.0000053 | 0.0000054 | 0.000003 |
| 6 | 0.000010 | 5.000000e−07 | 0.0000059 | 0.000024 | 0.000035 | 0.000043 |
| 6.5 | 0.000039 | 0.000026 | 0.000029 | 0.000087 | 0.000076 | 0.000079 |
| 7 | 0.00013 | 0.00014 | 0.00011 | 0.00019 | 0.00015 | 0.00015 |
| 7.5 | 0.00031 | 0.00031 | 0.00029 | 0.00036 | 0.00025 | 0.00019 |
| 8 | 0.00062 | 0.00061 | 0.00059 | 0.00057 | 0.00030 |  |

Where there are no data, there was no measurement made at that pH for that variant. Data is presented in initial velocity $V_0$ as OD/s.

Variants were tested for reversible deactivation following one hour exposures at a range of pHs. In general, some activity was detected in all variants exposed to pH>5, while others like V1, V3, V4 had appreciable activity at >3 pH (see Table 6). There was an apparent improvement in activity in some variants exposed to higher pHs, while other variants had similar activities at lower and higher pH exposures. For example there was a 4.3-6.6 fold increase in activity in variants V1 and V3 exposed at pH 6 versus pH 3. Other variants, including V4 and V5 have similar activities at pH 3 and pH 6, with overall 3.5-3.8 fold greater activity at pH 3 versus variants V1 and V3. The data suggest that some variants are reversibly deactivated at low pH and retain the ability to consume Phe when exposed to higher pH amenable to the intestinal environment, while others have an innate ability to retain activity at lower pHs that may also approximate the acidity of the gastric environment.

TABLE 6

Variant Activity Following Exposure to Low pH

| pH | V1 | V2 | V3 | V4 | V5 | V6 |
|---|---|---|---|---|---|---|
| 3 | 0.00012 | 0.000000 | 0.00012 | 0.00042 | 0.000045 | 0.000023 |
| 3.5 | 0.00055 | 0.00041 | 0.00032 | 0.00045 | 0.00018 | 0.000091 |
| 4 | 0.00056 | 0.00026 | 0.00026 | 0.00046 | 0.00033 | 0.00031 |
| 4.5 | 0.00063 | 0.00035 | 0.00034 | 0.00047 |  |  |
| 5 | 0.00064 | 0.00041 | 0.00042 | 0.00044 | 0.00027 | 0.00027 |
| 5.5 | 0.00070 | 0.00044 | 0.00047 | 0.00047 |  |  |
| 6 | 0.00079 | 0.00045 | 0.00051 | 0.00043 | 0.00031 | 0.00031 |
| 6.5 | 0.00084 | 0.00046 | 0.00052 | 0.00044 |  |  |
| 7 | 0.00056 | 0.00048 | 0.00054 | 0.00040 | 0.00031 | 0.00029 |
| 8 | 0.00063 | 0.00048 | 0.00052 | 0.00039 | 0.00033 | 0.00025 |

Where there are no data, there was no measurement made at that pH for that variant. Data is presented in initial velocity $V_0$ as OD/s.

Variants were tested in pepsin to assess their sensitivity to gastric protease digestion. Variants V1, V2, V3, and V4 did not lose appreciable activity after one hour exposure to pepsin indicating their resistance to digestion by the gastric protease (see Table 7). Variants V5 and V6 had lesser activity in pepsin and in the pepsin buffer, given their sensitivity to lower pH environments such as the pH 3.5 0.25M glycine buffer used for the pepsin assay.

TABLE 7

Variant Activity Following Exposure to Pepsin

| Time (s) | V1 −Pep | V1 +Pep | V2 −Pep | V2 +Pep | V3 −Pep | V3 +Pep | V4 −Pep | V4 +Pep | V5 −Pep | V5 +Pep | V6 −Pep | V6 +Pep |
|---|---|---|---|---|---|---|---|---|---|---|---|---|
| 0 | 0.14 | 0.12 | 0.13 | 0.11 | 0.12 | 0.11 | 0.14 | 0.14 | 0.082 | 0.069 | 0.074 | 0.070 |
| 15 | 0.15 | 0.14 | 0.14 | 0.12 | 0.13 | 0.11 | 0.14 | 0.15 | 0.084 | 0.069 | 0.075 | 0.070 |
| 30 | 0.16 | 0.15 | 0.15 | 0.13 | 0.14 | 0.12 | 0.14 | 0.15 | 0.086 | 0.069 | 0.077 | 0.070 |
| 45 | 0.17 | 0.17 | 0.16 | 0.13 | 0.14 | 0.12 | 0.14 | 0.15 | 0.088 | 0.069 | 0.076 | 0.069 |
| 60 | 0.18 | 0.17 | 0.16 | 0.14 | 0.14 | 0.13 | 0.14 | 0.15 | 0.090 | 0.072 | 0.077 | 0.069 |
| 75 | 0.19 | 0.18 | 0.17 | 0.15 | 0.15 | 0.13 | 0.15 | 0.16 | 0.091 | 0.069 | 0.078 | 0.069 |
| 90 | 0.20 | 0.19 | 0.17 | 0.15 | 0.16 | 0.14 | 0.15 | 0.16 | 0.093 | 0.070 | 0.078 | 0.069 |
| 105 | 0.20 | 0.20 | 0.18 | 0.16 | 0.16 | 0.14 | 0.15 | 0.16 | 0.096 | 0.070 | 0.079 | 0.069 |
| 120 | 0.21 | 0.21 | 0.18 | 0.16 | 0.17 | 0.15 | 0.15 | 0.16 | 0.097 | 0.070 | 0.079 | 0.069 |
| 135 | 0.22 | 0.21 | 0.19 | 0.17 | 0.17 | 0.15 | 0.16 | 0.17 | 0.10 | 0.070 | 0.080 | 0.069 |
| 150 | 0.22 | 0.22 | 0.19 | 0.1711 | 0.18 | 0.16 | 0.16 | 0.17 | 0.10 | 0.07 | 0.080 | 0.069 |
| 165 | 0.23 | 0.23 | 0.20 | 0.18 | 0.18 | 0.16 | 0.16 | 0.17 | 0.10 | 0.07 | 0.081 | 0.069 |
| 180 | 0.23 | 0.23 | 0.20 | 0.18 | 0.18 | 0.16 | 0.16 | 0.17 | 0.10 | 0.07 | 0.082 | 0.069 |
| 195 | 0.24 | 0.24 | 0.21 | 0.18 | 0.19 | 0.17 | 0.17 | 0.18 | 0.11 | 0.07 | 0.082 | 0.069 |
| 210 | 0.24 | 0.25 | 0.21 | 0.19 | 0.19 | 0.17 | 0.17 | 0.18 | 0.11 | 0.071 | 0.082 | 0.069 |
| 300 | 0.27 | 0.28 | 0.24 | 0.21 | 0.21 | 0.19 | 0.18 | 0.19 | 0.12 | 0.07 | 0.087 | 0.069 |
| 450 | 0.31 | 0.33 | 0.27 | 0.24 | 0.24 | 0.22 | 0.20 | 0.21 | 0.13 | 0.071 | 0.093 | 0.068 |
| 600 | 0.34 | 0.37 | 0.30 | 0.27 | 0.27 | 0.24 | 0.21 | 0.23 | 0.14 | 0.071 | 0.10 | 0.068 |

Data are presented in OD.

Variants were tested in chymotrypsin to assess their sensitivity to intestinal protease digestion. Variants overall did not lose appreciable activity after one hour exposure to chymotrypsin, with Variants V1, V2, V3 having the greatest activity levels (see Table 8). Variants V4, V5, and V6 displayed an apparent increase in activity after incubation in protease. Variant performance in trypsin was similar to that of chymotrypsin (data not shown).

TABLE 8

Variant Activity Following Exposure to Chymotrypsin

| Time (s) | V1 −Chy | V1 +Chy | V2 −Chy | V2 +Chy | V3 −Chy | V3 +Chy | V4 −Chy | V4 +Chy | V5 −Chy | V5 +Chy | V6 −Chy | V6 +Chy |
|---|---|---|---|---|---|---|---|---|---|---|---|---|
| 0 | 0.14 | 0.14 | 0.13 | 0.13 | 0.13 | 0.13 | 0.08 | 0.09 | 0.11 | 0.12 | 0.09 | 0.10 |
| 15 | 0.15 | 0.15 | 0.14 | 0.14 | 0.13 | 0.14 | 0.09 | 0.10 | 0.11 | 0.12 | 0.09 | 0.11 |
| 30 | 0.16 | 0.16 | 0.14 | 0.15 | 0.14 | 0.15 | 0.10 | 0.11 | 0.12 | 0.13 | 0.10 | 0.11 |
| 45 | 0.18 | 0.18 | 0.15 | 0.16 | 0.14 | 0.15 | 0.10 | 0.11 | 0.12 | 0.14 | 0.10 | 0.12 |
| 60 | 0.18 | 0.18 | 0.15 | 0.16 | 0.15 | 0.16 | 0.11 | 0.12 | 0.13 | 0.15 | 0.11 | 0.13 |
| 75 | 0.19 | 0.19 | 0.16 | 0.17 | 0.15 | 0.16 | 0.11 | 0.12 | 0.13 | 0.15 | 0.11 | 0.13 |
| 90 | 0.20 | 0.20 | 0.17 | 0.18 | 0.16 | 0.17 | 0.12 | 0.13 | 0.14 | 0.16 | 0.12 | 0.14 |
| 105 | 0.21 | 0.21 | 0.17 | 0.18 | 0.16 | 0.18 | 0.12 | 0.13 | 0.14 | 0.17 | 0.12 | 0.15 |
| 120 | 0.22 | 0.22 | 0.18 | 0.19 | 0.17 | 0.18 | 0.13 | 0.14 | 0.15 | 0.17 | 0.13 | 0.15 |
| 135 | 0.22 | 0.22 | 0.18 | 0.19 | 0.17 | 0.19 | 0.13 | 0.14 | 0.15 | 0.18 | 0.13 | 0.16 |
| 150 | 0.23 | 0.23 | 0.18 | 0.20 | 0.18 | 0.19 | 0.13 | 0.15 | 0.16 | 0.18 | 0.13 | 0.16 |
| 165 | 0.24 | 0.24 | 0.19 | 0.20 | 0.18 | 0.20 | 0.13 | 0.15 | 0.16 | 0.19 | 0.14 | 0.17 |
| 180 | 0.24 | 0.24 | 0.19 | 0.21 | 0.18 | 0.20 | 0.14 | 0.16 | 0.17 | 0.19 | 0.14 | 0.17 |
| 195 | 0.25 | 0.25 | 0.20 | 0.21 | 0.19 | 0.21 | 0.14 | 0.16 | 0.17 | 0.20 | 0.15 | 0.18 |
| 210 | 0.25 | 0.25 | 0.20 | 0.22 | 0.19 | 0.21 | 0.14 | 0.16 | 0.17 | 0.20 | 0.15 | 0.18 |
| 300 | 0.28 | 0.28 | 0.22 | 0.25 | 0.21 | 0.24 | 0.16 | 0.18 | 0.19 | 0.23 | 0.17 | 0.21 |
| 450 | 0.33 | 0.33 | 0.26 | 0.28 | 0.24 | 0.27 | 0.18 | 0.21 | 0.22 | 0.26 | 0.20 | 0.24 |
| 600 | 0.36 | 0.36 | 0.28 | 0.32 | 0.27 | 0.30 | 0.20 | 0.24 | 0.25 | 0.29 | 0.22 | 0.27 |

Data are presented in OD.

The relevant teachings of all patents, published applications and references cited herein are incorporated by reference in their entirety.

While this invention has been particularly shown and described with references to example aspects thereof, it will be understood by those skilled in the art that various changes in form and details may be made therein without departing from the scope of the invention encompassed by the appended claims.

What is claimed is:

1. A pharmaceutical formulation comprising a phenylalanine dehydrogenase polypeptide, or a functional fragment thereof, and a pharmaceutically-acceptable carrier, wherein the phenylalanine dehydrogenase polypeptide, or the functional fragment thereof, comprises an amino acid sequence having at least 80% sequence identity to SEQ ID NO: 1, wherein the pharmaceutical formulation is in a solid or semi-solid dosage form, or contained within an artificial membrane.

2. The pharmaceutical formulation of claim 1, wherein the formulation is in the form of a tablet.

3. The pharmaceutical formulation of claim 1, wherein the formulation is in the form of a capsule or a liquid.

4. The pharmaceutical formulation of claim 3, wherein the capsule is coated with a polymer that is resistant to acidic pH, degradation by digestive enzymes, or both.

5. The pharmaceutical formulation of claim 1, wherein the phenylalanine dehydrogenase polypeptide, or functional fragment thereof, is stable and active in the gastrointestinal tract of the subject.

6. The pharmaceutical formulation of claim 1, wherein the formulation is a sustained-release formulation.

7. The pharmaceutical formulation of claim 6, wherein the sustained-release formulation includes $NAD^+$ or an $NAD^+$ analog.

8. A method of reducing the level of phenylalanine in a subject in need thereof, comprising administering to the subject an effective amount of a phenylalanine dehydrogenase polypeptide, or a functional fragment thereof, wherein the phenylalanine dehydrogenase polypeptide or functional fragment thereof has at least about 80% sequence identity to SEQ ID NO: 1, and wherein the phenylalanine dehydrogenase polypeptide or functional fragment thereof is in a pharmaceutical formulation that is in a solid or semi-solid form, or contained within an artificial membrane.

9. The pharmaceutical formulation of claim 1, wherein the phenylalanine dehydrogenase polypeptide, or the functional fragment thereof, comprises SEQ ID NO: 6, SEQ ID NO: 7, SEQ ID NO: 8, SEQ ID NO: 9, SEQ ID NO: 10, or SEQ ID NO: 11.

10. A pharmaceutical formulation comprising a phenylalanine dehydrogenase polypeptide, or a functional fragment thereof, and a pharmaceutically-acceptable carrier, wherein the phenylalanine dehydrogenase polypeptide, or the functional fragment thereof, comprises an amino acid sequence having at least 80% sequence identity to SEQ ID NO: 1, and wherein the pharmaceutical formulation is in form of a tablet, suppository, pill, capsule, microsphere, powder, suspension, cream, ointment, or lotion.

11. The pharmaceutical formulation of claim 10, wherein the phenylalanine dehydrogenase polypeptide, or the functional fragment thereof, comprises SEQ ID NO: 6, SEQ ID NO: 7, SEQ ID NO: 8, SEQ ID NO: 9, SEQ ID NO: 10, or SEQ ID NO: 11.

12. The method of claim 8, wherein the level of phenylalanine is reduced in the blood of the subject.

13. The method of claim 8, wherein the subject has hyperphenylalaninemia.

14. The method of claim 8, wherein the phenylalanine dehydrogenase polypeptide has at least about 95% sequence identity to SEQ ID NO: 1.

15. The method of claim 8, wherein the phenylalanine dehydrogenase polypeptide, or functional fragment thereof, is administered orally.

16. The method of claim 8, wherein the phenylalanine dehydrogenase polypeptide, or functional fragment thereof, is delivered to the intestinal tract of the subject, to the blood of the subject, or a combination thereof.

17. The method of claim 8, further comprising administering an additional therapeutic agent to the subject.

18. The method of claim 17, wherein the additional therapeutic agent is a phenylalanine ammonia lyase enzyme, a large neutral amino acid (LNAA), or nicotinamide adenine dinucleotide ($NAD^+$).

19. The method of claim 8, wherein the subject has phenylketonuria (PKU).

20. The method of claim 8, wherein the phenylalanine dehydrogenase polypeptide comprises an amino acid sequence selected from the group consisting of SEQ ID NO: 6, SEQ ID NO: 7, SEQ ID NO: 8, SEQ ID NO: 9, SEQ ID NO: 10, and SEQ ID NO: 11.

* * * * *

SEQUENCE LISTING

<160> NUMBER OF SEQ ID NOS: 11

<210> SEQ ID NO 1

<211> LENGTH: 378
<212> TYPE: PRT
<213> ORGANISM: Geobacillus thermoglucosidasius

<400> SEQUENCE: 1

```
Met Asn Thr Val Thr Asn Gln Trp Lys Ala Val Asp Ile Phe Thr Gln
1               5                   10                  15

Ile Arg Asp His Glu Gln Val Val Phe Cys Asn Asp Lys Asn Thr Gly
            20                  25                  30

Leu Lys Ala Ile Ile Ala Ile His Asp Thr Thr Leu Gly Pro Ala Leu
        35                  40                  45

Gly Gly Cys Arg Met Tyr Pro Tyr Ala Thr Val Glu Asp Ala Leu Phe
    50                  55                  60

Asp Val Leu Arg Leu Ser Lys Gly Met Thr Tyr Lys Cys Leu Ala Ala
65                  70                  75                  80

Asp Val Asp Phe Gly Gly Gly Lys Ala Val Ile Ile Gly Asp Pro His
                85                  90                  95

Lys Asp Lys Thr Pro Glu Leu Phe Arg Ala Phe Gly Gln Phe Val Glu
            100                 105                 110

Ser Leu Asn Gly Arg Phe Tyr Thr Gly Thr Asp Met Gly Thr Thr Pro
        115                 120                 125

Asp Asp Phe Val His Ala Met Lys Glu Thr Asn Cys Ile Val Gly Val
    130                 135                 140

Pro Glu Glu Tyr Gly Gly Ser Gly Asp Ser Ser Val Pro Thr Ala Leu
145                 150                 155                 160

Gly Val Ile Tyr Gly Ile Gln Ala Thr Asn Lys Val Ile Trp Gly Ser
                165                 170                 175

Asp Glu Leu His Gly Lys Thr Tyr Ala Ile Gln Gly Leu Gly Lys Val
            180                 185                 190

Gly Arg Lys Val Ala Glu Arg Leu Leu Lys Glu Gly Ala Asp Leu Tyr
        195                 200                 205

Val Cys Asp Ile His Pro Thr Ala Ile Glu Ala Ile Val Ser Tyr Ala
    210                 215                 220

Lys Lys Leu Gly Ala Asn Val Lys Val Val Gln Gly Thr Glu Ile Tyr
225                 230                 235                 240

Arg Thr Asp Ala Asp Ile Phe Val Pro Cys Ala Phe Gly Asn Val Val
                245                 250                 255

Asn Asp Asn Thr Ile His Val Leu Lys Val Lys Ala Ile Val Gly Ser
            260                 265                 270

Ala Asn Asn Gln Leu Leu Asp Val Arg His Gly Gln Leu Leu Lys Glu
        275                 280                 285

Lys Gly Ile Leu Tyr Ala Pro Asp Tyr Ile Val Asn Ala Gly Gly Leu
    290                 295                 300

Ile Gln Val Ala Asp Glu Leu Tyr Gly Leu Asn Lys Glu Arg Val Leu
305                 310                 315                 320

Gln Lys Thr Lys Ala Ile Tyr Ser Thr Leu Leu His Ile Tyr Ser Arg
                325                 330                 335

Ala Glu Ala Asp His Ile Thr Thr Ile Glu Ala Ala Asn Arg Phe Cys
            340                 345                 350

Glu Glu Arg Leu Gln Gln Arg Ser Arg Arg Asn Asp Phe Phe Thr His
        355                 360                 365

Arg Lys Gln Pro Lys Trp Asp Ile Arg Arg
    370                 375
```

```
<210> SEQ ID NO 2
<211> LENGTH: 1137
<212> TYPE: DNA
<213> ORGANISM: Geobacillus thermoglucosidasius

<400> SEQUENCE: 2
atgaataccg ttaccaatca gtggaaagcg gtggatatat ttacgcaaat tcgtgaccat      60
gagcaagtcg tattttgtaa tgataaaaac acgggattaa aagcaattat cgccattcat     120
gacacaacgt taggcccagc gcttggcgga tgtcggatgt acccatatgc gaccgttgaa     180
gacgcactat ttgatgtgct ccgtctttcg aaagggatga cgtataaatg ccttgcggca     240
gatgtagatt ttggcggcgg caaagcggtt attatcggag acccgcacaa agacaagaca     300
ccggaattgt tccgtgcatt tggccagttt gttgaatcgt tgaatggccg gttttacaca     360
ggtactgata tgggaacgac gccggatgat ttcgttcacg cgatgaaaga aacaaactgc     420
atcgtaggtg ttcctgaaga gtatggcggc agcggcgatt cttcagtacc gaccgcgtta     480
ggtgtcattt acggtattca agctaccaat aaagtgattt ggggaagcga cgagcttcat     540
ggaaaaacgt acgccatcca agggttagga aaagtaggaa gaaagtagc ggagcgttta      600 ttgaaagaag gagcggactt gtatgtgtgc gatattcatc aacggcaat tgaagcgatt      660 gtatcatatg caaaaaaatt gggagcgaac gtaaaagttg tacaagggac ggaaatttac     720
agaacagacg cggatatatt tgttccatgt gcgttcggca atgttgtaaa tgataatacg     780
atacatgtgt tgaaagtaaa agcgattgtc ggttccgcca acaatcaatt acttgatgtg     840
cgccacggac agctgctgaa agagaaagga atttttatacg cgccagatta catcgttaac     900
gctggaggac ttattcaagt agctgatgag ctgtacggat tgaataaaga acgtgtacta     960
caaaaaacaa aagcgattta ttcgacgctc cttcatattt attcccgtgc agaagcagac    1020
catatcacaa caatcgaagc agcaaaccgt ttttgtgaag agcggttgca gcagcgtagc    1080
cgccgcaatg attttttttac gcaccgcaaa cagccgaagt gggatatccg ccggtaa      1137

<210> SEQ ID NO 3
<211> LENGTH: 1137
<212> TYPE: DNA
<213> ORGANISM: Artificial Sequence
<220> FEATURE:
<223> OTHER INFORMATION: Codon-Optimized Nucleotide Sequence

<400> SEQUENCE: 3
atgaatactg tgacgaatca atggaaagct gtcgatatct ttacgcagat ccgcgatcat      60
gaacaagttg ttttctgtaa tgataagaac accggtctga aggctatcat cgcgattcac     120
gacaccaccc tgggtcctgc tctgggcggc tgccgtatgt acccgtacgc gacggtcgaa     180
gatgccctgt tcgatgtcct gcgcctgagc aagggcatga cctacaagtg tttggcagct     240
gatgtagact ttggtggcgg caaagccgtg attatcggcg atccgcataa agataagacc     300
ccagagctgt tccgtgcatt tggtcagttt gtggagagcc tcaacggtcg tttctatacg     360
ggtaccgata tgggtaccac cccggacgac ttcgtgcacg cgatgaaaga aacgaactgc     420
attgtgggcg tcccggaaga gtatggtggc tcgggtgact ccagcgtccc gaccgcattg     480
ggcgtgatct acggcattca agcgaccaat aaagttatct ggggtagcga cgaactgcac     540
ggtaagactt acgcaatcca gggtctgggt aaggttggtc gtaaagtcgc agagcgcctg     600 ttgaagagg gtgcggacct gtatgtttgt gatattcacc cgacggcgat tgaagcgatc     660
gtgagctatg cgaagaaact gggtgcgaat gtcaaagtcg ttcagggtac ggaaatctat     720
```

```
cgcaccgacg cggacatttt cgtgccgtgc gcgttcggca atgttgtcaa cgataacact      780
attcatgttc tgaaagttaa ggcaatcgtt ggtagcgcga ataaccagct gctggacgtg      840
cgtcacggtc aactgctgaa agaaaagggc atcctgtatg ccccggatta cattgtgaac      900
gccggtggcc tgatccaagt cgcggacgaa ttataccggtc tgaacaaaga gcgcgttttg     960
caaaagacca aggcaatcta cagcaccctg ctgcacatct actctcgtgc cgaggcagac     1020
catattacca ccattgaagc cgcgaaccgt ttttgcgagg aacgcctgca gcaacgcagc     1080
agacgtaatg actttttcac gcaccgtaaa cagccgaaat gggatattcg tcgttaa        1137
```

<210> SEQ ID NO 4
<211> LENGTH: 38
<212> TYPE: DNA
<213> ORGANISM: Artificial Sequence
<220> FEATURE:
<223> OTHER INFORMATION: Forward Primer

<400> SEQUENCE: 4

```
tgtgctagca tgaataccgt taccaatcag tggaaagc                              38
```

<210> SEQ ID NO 5
<211> LENGTH: 32
<212> TYPE: DNA
<213> ORGANISM: Artificial Sequence
<220> FEATURE:
<223> OTHER INFORMATION: Reverse Primer

<400> SEQUENCE: 5

```
ctcgagtcat taccggcgga tatcccactt cg                                    32
```

<210> SEQ ID NO 6
<211> LENGTH: 378
<212> TYPE: PRT
<213> ORGANISM: Artificial Sequence
<220> FEATURE:
<223> OTHER INFORMATION: GtPheDH Variant 1 (V1)

<400> SEQUENCE: 6

```
Met Asn Thr Val Thr Asn Glu Trp Lys Ser Ala Asp Leu Phe Thr Gln
1               5                   10                  15

Met Arg Glu His Glu Gln Val Val Phe Cys Asn Asp Glu Lys Thr Gly
            20                  25                  30

Leu Lys Ala Ile Ile Ala Ile His Asn Thr Thr Leu Gly Pro Ala Leu
        35                  40                  45

Gly Gly Cys Arg Met Gln Pro Tyr Pro Thr Val Glu Ala Ala Leu Phe
    50                  55                  60

Asp Val Leu Arg Leu Ser Lys Gly Met Thr Tyr Lys Cys Ile Ala Ala
65                  70                  75                  80

Asp Val Asp Phe Gly Gly Gly Lys Ala Val Ile Ile Gly Asp Pro Arg
                85                  90                  95

Lys Asp Lys Ser Pro Glu Leu Phe Arg Ala Phe Gly Gln Phe Val Glu
            100                 105                 110

Ser Leu Asn Gly Arg Phe Tyr Thr Gly Thr Asp Met Gly Thr Thr Pro
        115                 120                 125

Glu Asp Phe Val His Ala Met Lys Glu Thr Asn Cys Ile Val Gly Val
    130                 135                 140

Pro Gln Glu Tyr Gly Gly Ser Gly Asp Ser Ser Val Pro Thr Ala Leu
145                 150                 155                 160

Gly Val Ile Tyr Gly Leu Gln Ala Thr Asn Lys Ala Leu Trp Gly Ser
```

```
                165                 170                 175
Asp Asp Leu Gln Gly Lys Thr Tyr Ala Ile Gln Gly Leu Gly Lys Val
            180                 185                 190

Gly Tyr Lys Val Ala Glu Gln Leu Leu Glu Lys Gly Ala Asn Leu Tyr
            195                 200                 205

Val Cys Asp Ile Asn Gln Ala Ala Val Asp Ser Ile Val Ser Tyr Ala
            210                 215                 220

Lys Glu Ile Gly Gly Ser Val Lys Val Val Asp Gly Asp Glu Ile Tyr
225                 230                 235                 240

Arg Thr Asp Ala Asp Val Phe Val Pro Cys Ala Phe Gly Asn Val Val
                245                 250                 255

Asn Asp Asp Thr Ile Asp Leu Phe Lys Val Lys Ala Ile Val Gly Ser
            260                 265                 270

Ala Asn Asn Gln Leu Leu Asp Val Arg His Gly Gln Met Leu Gln Glu
            275                 280                 285

Arg Gly Ile Leu Tyr Ala Pro Asp Tyr Ile Val Asn Ala Gly Gly Leu
            290                 295                 300

Ile Gln Val Ser Asp Glu Leu Tyr Gly Pro Asn Lys Glu Arg Val Leu
305                 310                 315                 320

Gln Lys Thr Lys Ala Ile Tyr Ser Thr Leu Leu Asp Ile Tyr Thr Gln
                325                 330                 335

Ala Glu Asn Glu Gln Leu Thr Thr Ile Glu Ala Ala Asn Arg Phe Cys
            340                 345                 350

Glu Asn Arg Leu Glu Met Arg Ser Arg Arg Asn Asn Phe Phe Ser His
            355                 360                 365

Lys Lys Arg Pro Lys Trp Asp Ile Arg Leu
            370                 375

<210> SEQ ID NO 7
<211> LENGTH: 378
<212> TYPE: PRT
<213> ORGANISM: Artificial Sequence
<220> FEATURE:
<223> OTHER INFORMATION: GtPheDH Variant 2 (V2)

<400> SEQUENCE: 7

Met Asn Thr Val Thr Asn Glu Trp Lys Ser Ala Asp Leu Phe Thr Gln
1               5                   10                  15

Met Arg Glu His Glu Gln Val Val Phe Cys Asn Asp Glu Lys Thr Gly
            20                  25                  30

Leu Lys Ala Ile Ile Ala Ile His Asn Thr Thr Leu Gly Pro Ala Leu
        35                  40                  45

Gly Gly Cys Arg Met Gln Pro Tyr Pro Thr Val Glu Ala Ala Leu Phe
    50                  55                  60

Asp Val Leu Arg Leu Ser Lys Gly Met Thr Tyr Lys Cys Ile Ala Ala
65                  70                  75                  80

Asp Val Asp Phe Gly Gly Gly Lys Ala Val Ile Ile Gly Asp Pro Arg
                85                  90                  95

Lys Asp Lys Ser Pro Glu Leu Phe Arg Ala Phe Gly Gln Phe Val Glu
            100                 105                 110

Ser Leu Asn Gly Arg Phe Tyr Thr Gly Thr Asp Met Gly Thr Thr Pro
            115                 120                 125

Glu Asp Phe Val His Ala Met Lys Glu Thr Asn Cys Ile Val Gly Val
            130                 135                 140

Pro Gln Glu Tyr Gly Gly Ser Gly Asp Ser Ser Val Pro Thr Ala Leu
```

```
                145                 150                 155                 160
Gly Val Ile Tyr Gly Leu Gln Ala Thr Asn Lys Ala Leu Trp Gly Ser
                    165                 170                 175

Asp Asp Leu Gln Gly Lys Thr Tyr Ala Ile Gln Gly Leu Gly Lys Val
                    180                 185                 190

Gly Tyr Lys Val Ala Glu Gln Leu Leu Glu Lys Gly Ala Asp Leu Tyr
                    195                 200                 205

Val Cys Asp Ile Asn Gln Ala Ala Val Asp Ser Ile Val Ser Tyr Ala
                    210                 215                 220

Lys Glu Ile Gly Gly Ser Val Lys Val Val Asp Gly Asp Glu Ile Tyr
225                 230                 235                 240

Arg Thr Asp Ala Asp Val Phe Val Pro Cys Ala Phe Gly Asn Val Val
                    245                 250                 255

Asn Asp Asp Thr Ile Asp Leu Phe Lys Val Lys Ala Ile Val Gly Ser
                    260                 265                 270

Ala Asn Asn Gln Leu Leu Asp Val Lys His Gly Gln Met Leu Gln Glu
                    275                 280                 285

Lys Gly Ile Leu Tyr Ala Pro Asp Tyr Ile Val Asn Ala Gly Gly Leu
                    290                 295                 300

Ile Gln Val Ser Asp Glu Leu Tyr Gly Pro Asn Lys Glu Arg Val Leu
305                 310                 315                 320

Gln Lys Thr Lys Ala Ile Tyr Ser Thr Leu Leu Asp Ile Tyr Thr Gln
                    325                 330                 335

Ala Glu Asn Glu Gln Leu Thr Thr Ile Glu Ala Ala Asn Arg Phe Cys
                    340                 345                 350

Glu Asn Arg Leu Glu Met Arg Ser Arg Arg Asn Asn Phe Phe Ser His
                    355                 360                 365

Lys Lys Arg Pro Lys Trp Asp Ile Arg Leu
                    370                 375

<210> SEQ ID NO 8
<211> LENGTH: 378
<212> TYPE: PRT
<213> ORGANISM: Artificial Sequence
<220> FEATURE:
<223> OTHER INFORMATION: GtPheDH Variant 3 (V3)

<400> SEQUENCE: 8

Met Asn Thr Val Thr Asn Glu Trp Lys Ser Ala Asp Leu Phe Thr Gln
1               5                   10                  15

Met Arg Glu His Glu Gln Val Val Phe Cys Asn Asp Glu Lys Thr Gly
                20                  25                  30

Leu Lys Ala Ile Ile Ala Ile His Asn Thr Thr Leu Gly Pro Ala Leu
            35                  40                  45

Gly Gly Cys Arg Met Gln Pro Tyr Pro Thr Val Glu Ala Ala Leu Phe
50                  55                  60

Asp Val Leu Arg Leu Ser Lys Gly Met Thr Tyr Lys Cys Ile Ala Ala
65                  70                  75                  80

Asp Val Asp Phe Gly Gly Gly Lys Ala Val Ile Ile Gly Asp Pro Arg
                85                  90                  95

Lys Asp Lys Ser Pro Glu Leu Phe Arg Ala Phe Gly Gln Phe Val Glu
            100                 105                 110

Ser Leu Asn Gly Arg Phe Tyr Thr Gly Thr Asp Met Gly Thr Thr Pro
        115                     120                 125

Glu Asp Phe Val His Ala Met Lys Glu Thr Asn Cys Ile Val Gly Val
```

```
                130                 135                 140
Pro Gln Glu Tyr Gly Gly Ser Gly Asp Ser Ser Val Pro Thr Ala Leu
145                 150                 155                 160

Gly Val Ile Tyr Gly Leu Gln Ala Thr Asn Lys Ala Leu Trp Gly Ser
                165                 170                 175

Asp Asp Leu Gln Gly Lys Thr Tyr Ala Ile Gln Gly Leu Gly Lys Val
                180                 185                 190

Gly Tyr Lys Val Ala Glu Gln Leu Leu Glu Lys Gly Ala Asn Leu Tyr
            195                 200                 205

Val Cys Asp Ile Asn Gln Ala Ala Val Asp Ala Ile Val Ser Tyr Ala
        210                 215                 220

Lys Glu Ile Gly Gly Ser Val Lys Val Val Asp Gly Asp Glu Ile Tyr
225                 230                 235                 240

Arg Thr Asp Ala Asp Val Phe Val Pro Cys Ala Phe Gly Asn Val Val
                245                 250                 255

Asn Asp Asp Thr Ile Asp Leu Leu Lys Val Lys Ala Ile Val Gly Ser
                260                 265                 270

Ala Asn Asn Gln Leu Leu Asp Val Arg His Gly Gln Met Leu Gln Glu
            275                 280                 285

Arg Gly Ile Leu Tyr Ala Pro Asp Tyr Ile Val Asn Ala Gly Gly Leu
        290                 295                 300

Ile Gln Val Ser Asp Glu Leu Tyr Gly Pro Asn Lys Glu Arg Val Leu
305                 310                 315                 320

Gln Lys Thr Lys Ala Ile Tyr Ser Thr Leu Leu Asp Ile Tyr Ala Gln
                325                 330                 335

Ala Glu Asn Glu Gln Leu Thr Thr Ile Glu Ala Ala Asn Arg Phe Cys
                340                 345                 350

Glu Asn Arg Leu Glu Met Arg Ser Arg Arg Asn Asn Phe Phe Ser His
            355                 360                 365

Lys Lys Arg Pro Lys Trp Asp Ile Arg Leu
        370                 375

<210> SEQ ID NO 9
<211> LENGTH: 378
<212> TYPE: PRT
<213> ORGANISM: Artificial Sequence
<220> FEATURE:
<223> OTHER INFORMATION: GtPheDH Variant 4 (V4)

<400> SEQUENCE: 9

Met Asn Thr Val Thr Asn Glu Trp Lys Ser Ala Asp Leu Phe Thr Gln
1               5                   10                  15

Met Arg Glu His Glu Gln Val Val Phe Cys Asn Asp Glu Lys Thr Gly
                20                  25                  30

Leu Lys Ala Ile Ile Ala Ile His Ser Thr Thr Leu Gly Pro Ala Leu
            35                  40                  45

Gly Gly Cys Arg Met Gln Pro Tyr Pro Thr Val Glu Ala Ala Leu Phe
        50                  55                  60

Asp Val Leu Arg Leu Ser Lys Gly Met Thr Tyr Lys Cys Ile Ala Ala
65                  70                  75                  80

Asp Val Asp Phe Gly Gly Gly Lys Ala Val Ile Ile Gly Asp Pro Arg
                85                  90                  95

Lys Asp Lys Ser Pro Glu Leu Phe Arg Ala Phe Gly Gln Phe Val Glu
            100                 105                 110

Ser Leu Asn Gly Arg Phe Tyr Thr Gly Thr Asp Met Gly Thr Thr Pro
```

```
                115              120              125
    Glu Asp Phe Val His Ala Met Lys Glu Thr Asn Cys Ile Val Gly Val
    130                 135                 140

Pro Gln Glu Tyr Gly Gly Ser Gly Asp Ser Ser Val Pro Thr Ala Leu
145                 150                 155                 160

Gly Val Ile Tyr Gly Leu Gln Ala Thr Asn Lys Ala Leu Trp Gly Ser
                    165                 170                 175

Asp Asp Leu Gln Gly Lys Thr Tyr Ala Ile Gln Gly Leu Gly Lys Val
                180                 185                 190

Gly Tyr Lys Val Ala Glu Gln Leu Leu Glu Lys Gly Ala Asn Leu Tyr
            195                 200                 205

Val Cys Asp Ile Asn Gln Ala Ala Val Asp Ala Ile Val Ser Tyr Ala
        210                 215                 220

Lys Glu Ile Gly Gly Ser Val Lys Val Val Asp Gly Asp Glu Ile Tyr
    225                 230                 235                 240

Ser Thr Asp Ala Asp Val Phe Val Pro Cys Ala Phe Gly Asn Val Val
                    245                 250                 255

Asn Asp Asp Thr Ile Asp Leu Leu Lys Val Lys Ala Ile Val Gly Ser
                260                 265                 270

Ala Asn Asn Gln Leu Leu Asp Val Arg His Gly Gln Met Leu Gln Glu
            275                 280                 285

Arg Gly Ile Leu Tyr Ala Pro Asp Tyr Ile Val Asn Ala Gly Gly Leu
        290                 295                 300

Ile Gln Val Ser Asp Glu Leu Tyr Gly Pro Asn Lys Glu Arg Val Leu
    305                 310                 315                 320

Gln Lys Thr Lys Ala Ile Tyr Ser Thr Leu Gln Asn Ile Tyr Ala Gln
                    325                 330                 335

Ala Glu Asn Glu Gln Leu Thr Thr Ile Glu Ala Ala Asn Arg Phe Cys
                340                 345                 350

Glu Asn Arg Leu Glu Ala Arg Ser Arg Arg Asn Asn Phe Phe Ser His
            355                 360                 365

Lys Lys Arg Pro Lys Trp Asp Ile Arg Leu
        370                 375

<210> SEQ ID NO 10
<211> LENGTH: 378
<212> TYPE: PRT
<213> ORGANISM: Artificial Sequence
<220> FEATURE:
<223> OTHER INFORMATION: GtPheDH Variant 5 (V5)

<400> SEQUENCE: 10

Met Asn Thr Val Thr Asn Glu Trp Lys Ser Ala Asp Leu Phe Thr Gln
1               5                   10                  15

Met Arg Glu His Glu Gln Val Val Phe Cys Asn Asp Glu Ala Thr Gly
                20                  25                  30

Leu Lys Ala Ile Ile Ala Ile His Ser Thr Thr Leu Gly Pro Ala Leu
            35                  40                  45

Gly Gly Cys Arg Met Gln Pro Tyr Pro Thr Val Glu Ala Ala Leu Phe
        50                  55                  60

Asp Val Leu Arg Leu Ser Lys Gly Met Thr Tyr Lys Cys Ile Ala Ala
65                  70                  75                  80

Asp Val Asp Phe Gly Gly Gly Lys Ala Val Ile Ile Gly Asp Pro Arg
                85                  90                  95

Lys Asp Lys Ser Pro Glu Leu Phe Arg Ala Phe Gly Gln Phe Val Glu
```

```
              100                 105                 110
Ser Leu Asn Gly Arg Phe Tyr Thr Gly Thr Asp Met Gly Thr Thr Pro
        115                 120                 125

Glu Asp Phe Val His Ala Met Lys Glu Thr Asn Cys Ile Val Gly Val
130                 135                 140

Pro Gln Glu Tyr Gly Ser Gly Asp Ser Ser Ile Pro Thr Ala Leu
145                 150                 155                 160

Gly Val Ile Tyr Gly Leu Gln Ala Thr Asn Lys Ala Leu Trp Gly Ser
                165                 170                 175

Asp Asp Leu Gln Gly Lys Thr Tyr Ala Ile Gln Gly Leu Gly Lys Val
            180                 185                 190

Gly Tyr Lys Val Ala Glu Gln Leu Leu Glu Lys Gly Ala Asn Leu Tyr
        195                 200                 205

Val Cys Asp Ile Asn Gln Ala Ala Val Asp Ala Ile Val Ser Tyr Ala
    210                 215                 220

Lys Glu Ile Gly Gly Ser Val Lys Val Val Asp Gly Asp Glu Ile Tyr
225                 230                 235                 240

Ser Thr Asp Ala Asp Val Phe Val Pro Cys Ala Phe Gly Asn Val Val
                245                 250                 255

Asn Asp Asp Thr Ile Asp Leu Leu Lys Val Lys Ala Ile Val Gly Ser
            260                 265                 270

Ala Asn Asn Gln Leu Leu Asp Val Arg His Gly Gln Met Leu Gln Glu
        275                 280                 285

Arg Gly Ile Leu Tyr Ala Pro Asp Tyr Ile Val Asn Ala Gly Gly Leu
    290                 295                 300

Ile Gln Val Ser Asp Glu Leu Tyr Gly Pro Asn Lys Glu Arg Val Leu
305                 310                 315                 320

Gln Lys Thr Lys Ala Ile Tyr Ser Thr Leu Gln Asn Ile Tyr Ala Gln
                325                 330                 335

Ala Glu Asn Glu Gln Leu Thr Thr Ile Glu Ala Ala Asn Gln Phe Cys
            340                 345                 350

Glu Asn Arg Leu Glu Ala Arg Ser Arg Arg Asn Asn Phe Phe Ser His
        355                 360                 365

Lys Lys Arg Pro Lys Trp Asp Ile Arg Leu
    370                 375

<210> SEQ ID NO 11
<211> LENGTH: 378
<212> TYPE: PRT
<213> ORGANISM: Artificial Sequence
<220> FEATURE:
<223> OTHER INFORMATION: GtPheDH Variant 6 (V6)

<400> SEQUENCE: 11

Met Asn Thr Val Thr Asn Glu Trp Lys Ser Ala Asp Leu Phe Thr Gln
1               5                   10                  15

Met Arg Glu His Glu Gln Val Val Phe Cys Asn Asp Glu Lys Thr Gly
            20                  25                  30

Leu Lys Ala Ile Ile Ala Ile His Ser Thr Thr Leu Gly Pro Ala Leu
        35                  40                  45

Gly Gly Cys Arg Met Gln Pro Tyr Pro Thr Val Glu Ala Ala Leu Phe
    50                  55                  60

Asp Val Leu Arg Leu Ser Lys Gly Met Thr Tyr Lys Cys Ile Ala Ala
65                  70                  75                  80

Asp Val Asp Phe Gly Gly Gly Lys Ala Val Ile Ile Gly Asp Pro Arg
```

-continued

```
                     85                      90                      95
Lys Asp Lys Ser Pro Glu Leu Phe Arg Ala Phe Gly Gln Phe Val Glu
            100                     105                 110

Ser Leu Asn Gly Arg Phe Tyr Thr Gly Thr Asp Met Gly Thr Thr Pro
            115                     120                 125

Glu Asp Phe Val His Ala Met Lys Glu Thr Asn Cys Ile Val Gly Val
            130                     135                 140

Pro Gln Glu Tyr Gly Gly Ser Gly Asp Ser Ser Val Pro Thr Ala Leu
145                     150                     155                 160

Gly Val Ile Tyr Gly Leu Gln Ala Thr Asn Lys Ala Leu Trp Gly Ser
                165                     170                 175

Asp Asp Leu Gln Gly Lys Thr Tyr Ala Ile Gln Gly Leu Gly Lys Val
            180                     185                 190

Gly Ala Lys Val Ala Glu Gln Leu Leu Glu Lys Gly Ala Asn Leu Tyr
            195                     200                     205

Val Cys Asp Ile Asn Gln Ala Ala Val Asp Ala Ile Val Ser Tyr Ala
            210                     215                 220

Lys Glu Ile Gly Gly Ser Ile Lys Val Val Asp Gly Asp Glu Ile Tyr
225                     230                     235                 240

Ser Thr Asp Ala Asp Val Phe Val Pro Cys Ala Phe Gly Asn Val Val
                245                     250                 255

Asn Asp Asp Thr Ile Asp Leu Leu Lys Val Lys Ala Ile Val Gly Ser
            260                     265                 270

Ala Asn Asn Gln Leu Leu Asp Val Arg His Gly Gln Met Leu Gln Glu
            275                     280                     285

Arg Gly Ile Leu Tyr Ala Pro Asp Tyr Ile Val Asn Ala Gly Gly Leu
            290                     295                 300

Ile Gln Val Ser Asp Glu Leu Tyr Gly Pro Asn Lys Glu Arg Val Leu
305                     310                     315                 320

Gln Lys Thr Lys Ala Ile Tyr Ser Thr Leu Gln Asn Ile Tyr Ala Gln
            325                     330                     335

Ala Glu Asn Glu Gln Leu Thr Thr Ile Glu Ala Ala Asn Gln Phe Cys
            340                     345                     350

Glu Asn Arg Leu Glu Ala Arg Ser Arg Arg Asn Asn Phe Phe Ser His
            355                     360                     365

Lys Lys Arg Pro Lys Trp Asp Ile Arg Leu
            370                     375
```